United States Patent
Brooks

(10) Patent No.: US 8,609,158 B2
(45) Date of Patent: Dec. 17, 2013

(54) DIANE'S MANNA

(76) Inventor: Diane Elizabeth Brooks, Sandy, OR (US)

( * ) Notice: Subject to any disclaimer, the term of this patent is extended or adjusted under 35 U.S.C. 154(b) by 0 days.

(21) Appl. No.: 13/507,308

(22) Filed: Jun. 20, 2012

(65) Prior Publication Data

US 2013/0017269 A1    Jan. 17, 2013

Related U.S. Application Data

(60) Provisional application No. 61/572,088, filed on Jul. 11, 2011.

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS 7,348,035 B2 *    3/2008   Schleifenbaum et al. .... 426/534

\* cited by examiner

*Primary Examiner* — Michael Meller

(57) ABSTRACT

This is a potent drug with narcotic benefits made from distinctly and uniquely combined and processed interchangeable seed and seed derivatives that are so potent that it removes or alleviates depression, mood disorders, Attention Disorder symptoms, thought disorder, mental illness, pain, right lip retardation symptoms, physical problems, Lymph Node cancer and many other illness symptoms. It removes bumps in the neck within a week or two. It is interchangeable in most aspects. It can be combined and processed with Pharmaceuticals and medicines to create new drugs. These Pharmaceuticals are now long lasting. I prefer the daily dose, but this drug can last months. It is extremely strong or potent and can be made weak to make your little Attention deficit child normal. It is an incredible mood stabilizer and reduces psychosis. Use it for cancer patient and for people with pain issues. It works.

1 Claim, No Drawings

DIANE'S MANNA

BACKGROUND OF THE INVENTION

This medicine is a continual drug made from interchangeable ingredients that heals and alleviates the symptoms of many illnesses including cancer and mental illness and pain and many others with the unique benefit it can be combined with medicines like Zyprexa with the benefit of this combination lasting months with a extremely strong, narcotic in nature and easily tamed medicinal benefit for over 21 days.

Although please understand, I don't need to add Zyprexa or Ibuprofen to this medicine because it is good enough to do the job without adding any medicine to it.

BACKGROUND TO THE SPECIFICATION

This is a food. I used basic food to make this drug. You can use the plants and ingredients from the backyard, the field, or the grocery store to make this drug. This is a medicine that continues inside the human and animal body that will work on most or many symptoms in Exhibit A. Exhibit A and B are a complete or mostly complete list of mine and Micah's illness symptoms. I started with simple 1 to 3 ingredients combinations of which were all interchangeable, even the processes were interchangeable. Exhibit G has a combination that is so strong after you quit taking it, that every drug manufacturer on this planet will be wanting to kill me. I did it. It is a food combination. This is a food that can be interchanged with many other like kind ingredients. The processes used are many, but I sampled all of them and eliminated many of the side-effects by eliminating combinations that do not work. It is a processed drug. It is a drug. I spent almost 6 years sampling and changing these to make one interchangeable ingredient great one (with many variations) in best methods exhibit and favorite best methods exhibit and have used hundreds and written thousands. They all are good, but some are better than others. The interchangeability of this drug and the number of interchangeability and processing of ingredients up to 7 is so crucial to making strong or weak drugs and the 7 ingredient combination makes this drug continually medicate the body and it can make other medicines continue also. I can use 3 ingredients, 1 or 7, other combinations and more additions and processes them all many ways.

I am a minister who has prayed my way through this medicine.

BRIEF SUMMARY OF INVENTION

I am showing everyone how easy it is to make 1-7 Interchangeable ingredients heal and alleviate the symptoms of many illnesses. It is a unique list of interchangeable ingredients and has unique continuing abilities, extreme potencies, narcotic effects, symptom alleviating abilities, food combinations and food and medicine combinations that have to be patented. I used many processes and the simple ones in the best methods and my favorite best methods show how easy it is to heal and alleviate many forms of mental illness. I simply do not have many problems with my severe right lip retardation anymore and my pain is almost gone. Cancer is no longer a threat. I live with great and happy moods and have absolutely no depression on this medicine. It is a great mood stabilizer, but does have narcotic effects. It is a continual medicine or a daily dose medicine. Both work. I have even added it to many medicines and it made those medicines continue also. I also eliminated bumps in my daughters neck within less than 2 weeks, that Dr's tried for 1½ years and couldn't get rid of I was scared because I had Lymph node cancer and was convinced my 5 year old had the same cancer. The process and method I used on my daughter was simply a food formula of this patent pending. I used a much stronger version of this medicine to medicate myself after I was diagnosed with Lymph node cancer. I refused my second surgery and daily treated myself with these processed ingredients. The Dr. was scheduled to cut open my entire neck and gut out all my upper lymph nodes and tonsils and whatever else he found, then chemo me and radiate me. I said no. He said it was in my calls. Well, my treatment works great. It is 4½ years after my lymph node cancer was found and I have no signs of cancer. It is a cancer remover. It can be used with cancer treatments and can push out cancer. It should be used with other illnesses.

Contents

Provisional Info: 61/572,088

Diane's Manna and a Provisional Filing Label receipt number: EG54 7208 347U S received on Jul. 13, 2011 at 3:00 pm Express mail Delivered to ALEXANDRIA, VA 22313 to PATENT OFFICE 22313.

Filed on Jul. 11, 2011 by The Office of Overseer, Diane Brooks and Her Successors, A Corporate Sole for Children's Fund, (D.B.A Children's Fund)

By Diane Brooks Provisional Date: Jul. 11, 2011.

Background of the Invention p. 1-2, Brief Summary of the Invention p. 3,

Abstract of the Disclosure p. 4 Contents p. 5

Claims p. 6-15

Description Specification (1 through page 105) p. 1-49

Exhibit A: Symptoms of Diane Brooks and Symptoms, Illnesses and Issues (many of these are alleviated with this medicine; p. 50-57

Exhibit B: Doctors diagnosis of Diane and Micah Brooks; p. 58-61

Exhibit C: Sample Ways this patent can be used; p; 62-64

Exhibit D: Best Methods; p. 65-78

Exhibit E: Processes Samples and just a few processes; p. 79

Exhibit F: Interchangeable Ingredients Samples and just a few samples; p. 80-82

Exhibit G: My favorite Best Method and Uncooked Version p. 83-93 (It is good for my symptoms and Micah's too);

Exhibit H: Prior Art and with Information disclosure (25 additional pages) p. 94-96 Additional 25 pages with Information disclosure Statement Exhibit I: Statement of Use; p. 97-101, Extras p. 102-108, Summary 109

The method of healing the body, Benefiting, feeding, reducing, detoxifying, Increasing or decreasing in potency, decreasing illness symptoms, Increasing or decreasing in strength, Changing, Anesthetizing, slowing down, Relaxing, Improving, Stabilizing, Relieving, medicating, continuing or not continuing in a continuum, a food continuing or not continuing, decreasing, burning, pushing out, removing, regulating, sedating, helping, fueling, giving Analgesic benefit, giving Narcotic benefit, and Alleviating the symptoms and what is listed in Exhibit A and Exhibit B Doctor list with interchangeable food, interchangeable processed ingredients, interchangeable pharmaceutical drugs, interchangeable non-pharmaceutical drugs, interchangeable combined Pharmaceutical drugs with these interchangeable ingredients, interchangeable plants, interchangeable seeds, interchangeable Derivatives of Seed, interchangeable organism or human fluids and interchangeable parts, earth ingredients, sub-classes of patents, interchangeable processes, interchangeable methods of use, interchangeable uses, that are Interchangeable and each have their own individual uses, combined uses, methods of use, methods of ingestion, claims and benefits.

Please refer to Exhibit A to see a list of what this patent alleviates on me.

These symptoms are listed in claim 1.

Seed and what comes from a seed (Seed Derivatives) burned cancer out of me. You can use an Evening Primrose oil and Olive Oil. I used a strong doses of processed Evening Primrose Oil.

An Example of what this can do:

Example: I am almost normal when I take my favorite best method. I refused my surgery for Lymph Node cancer. The doctor wanted to take my all my upper Lymph nodes, a spot on my thyroid, and remove my tonsils and anything else he felt he needed to remove. I refused surgery, chemotherapy and radiation for cancer to find the primary origin of a removed fast growing tumor 4 years ago and treated myself with this patent. I have virtually eliminated my mood disorder. I have virtually eliminated my mind disorder. I have almost completely eliminated my lip retardation. I have a healthy blood flow and the grains are continually benefiting my health. I have greatly reduced delusions. I rarely have pain with higher seed and caffeine potencies and subdued pain with lower potencies. I had back and neck pain for 25 years. I almost never have back pain now. I almost completely eliminated my headaches that I have had since I was 2. I have no noticeable Premenstrual syndrome symptoms or Menopause symptoms except for minor hot flashes. I was diagnosed Bi-Polar and these symptoms are just plain simple to remove. Bi-Polar is a problem. I made it no problem. As one example, I add Ibuprofen (800 mg max) and in the morning and afternoon, after a couple of cups of coffee and my regular daily dose of my best methods, I am extremely sedated and these additional medications or added drugs are amplified and make this drug more potent and can be dangerous if you add strong medicines to these without testing the amplified rate of medicinal value. I can easily make over the counter drugs or Pharmaceutical drugs more potent and last longer than their normal rates. I give you combinations and processed specific drugs. It is a food that when you combine it and eat it or process it, you mostly subdue or eliminate many symptoms of many illnesses. The important sub-structure of this medicine is a seed, seed derivative and a medicine that is interchangeable. One example is: Sesame seed, green tea and milk cooked the same as in the best methods Exhibits D and G.

Please use the dictionary definitions of "Seed" and "Derivative". That way you can get a clear picture of how I use the terms Seed and Seed Derivative.

This is a very unique patent. I specifically used certain ingredients at certain measurements and at certain temperatures to create these. I can change the quantities and qualities and processes. Even though I can interchange them and make them last, I used a very certain combination. It is imperative that you understand the exact combinations do what I have claimed.

You must detoxify with the food version and simple food recipes for best results (afterwards or when you want to get off these medicines or recipes) if you take my best methods. You create a continuing drug in your body by using these methods. It looks like a harmless or a basic food recipe that simply cannot do this You will get extremely medicated and it can cause an increased intoxication if you stop taking this. An example of a detoxification food is: You must eat cups of rice, a few tsps of cheese, 2 tsps of green beans, hot milk and very little coffee or caffeine if you need to lower your intoxication. It is mandatory to lower drastically your caffeine intake for extreme overdoses. Do it many, many, many days. You could also eat many greens, but it causes too rapid of a detoxification and can cause psychosis. This drug is continual. You should remove the medicine this way. This is a warning.

DESCRIPTION

To the Paranoid Delusional and the Chronically Mentally Ill and Those Afflicted with Illness and Illness Symptoms in Exhibit A Go straight to Exhibit G (my favorite best method cooked versions) and make it immediately. Take it in cups or $\frac{3}{4}^{th}$ cups large doses with hot milk (and oil as directed) in the morning and afternoon for days then taper it off until you get to a lower dose. Drink 2 cups of coffee. In the late morning I drink ½ cup of coffee and ½ cup of milk or green tea. Make this a daily medicine. You must acclimate this food/medicine in your body and keep it in you daily. It is an easy, in your kitchen food, that will help you in 1-10 days and it will help eliminate any hospital trip. After 2-4 weeks, slowly reduce the quantity gradually and lower the medication to a tablespoon per day as directed, you will see the medication effect. You must eat cups at first for many, many days. You must have your body acclimated on this drug. I have you my friend. I have your sanity. If you want, add one glass of red wine or 4 little fruit figs or fruits or dates, a little meat and watch this medicine be better. For a good recipe, drink ½ cup of evaporated milk before bedtime. (For regular medicinal benefits: Do not eat a lot of green plants/seeds on this medicine. Stay away from excess greens if you are not balanced in your foods.) It pushes out your medicine and causes a detoxification. I eat green plants, but I hate my medicine balance right after that or many hours later. It takes a day to rebalance. It is not worth the psychosis or little pains that pop through. (It should be noted that I eat sushi and seaweed is on the rice and I eat soy beans. This is balanced by the rice and green tea and the meat or fish.)

You will not need to make major adjustments in this recipe. The major adjustment you must make is to understand that a coffee or tea drinker or someone who has a daily intake of caffeine will be using different drug or food than someone who has zero caffeine intake daily. These are made based on my daily intake of coffee. I use 3 cups of coffee approximately in the morning and one in the afternoon, maybe. 1 at night can be consumed (and add a little evaporated milk or creamer) if you need to make this food stronger. You must adjust these for that issue. I have spent 5 years adjusting these doses and finding a combination that works best. You do not want to adjust these too much. Mix it in perfect quantities (not too far off from the quantities I have listed and you will have a well balanced medicine.) You actually can make many changes, but the best methods are a good example to get you to the right quantities. The ingredients can all be adjusted. The problem is too much of one ingredient or too little of one ingredient affects the others adversely. Another problem or benefit is length of cooking time and how you process these ingredients. This 1 best method and my favorite recipes have been tested over and over again and I have found these exact quantities and this exact processing to be my favorite. You need a balance. The 1 best method and my favorite best method will work for most of your issues. You can make many different versions and I did. I am giving you a best method that has eliminated most of the side effects I have experienced. The combination is the one I would call my personal favorite (Unless I made it a little weaker. Too strong of a medicine and people cannot drive to work and operate normal day to day lives.) Let us keep our people safe. I do not claim this to be the only method. I have many other recipes.

(You should detoxify on my detoxification recipe after you use best method recipes. The best method is to use unleavened bread biblically. That would be wheat, water and a little oil. Eat a bunch. You can also just eat wheat flour mixed with water and a little oil. If you do not detoxify, the imbalances can affect you adversely. You can actually get very high by not using very much of the medicine. A best method to detoxify or purge your body is to eat 1-2 cups of rice cooked, a little cheese, milk, a little greens and a processed seed/caffeine/milk if you need it. It should be done daily to move out the medicine and replace your cells with a clean, no medicine daily dose. I sometimes lower my favorite best methods potencies and the reduction in sesame seeds or caffeine is an overdose if the previous best method I took was not purged out correctly. The 1 best method is to eat cups of the new best method for many, many days to reacclimatize your cells with the new medicine or when you finally do lower your dose to a tablespoon per day of the best method and you find you are extremely medicated and need a reduction in the drug, I simply eat normal but I use a lot of cooked rice or wheat and a little greens and a little cheese and a lot of milk. It is a purging process. I continue a tablespoon of my new lower potency 1 best method and a cup or more of a rice or wheat and oil to help me acclimate to my new medicine. The other way is to just completely detoxify before using a new, lower dose or lower potency 1 best method or my favorite best method. Another way to lower your dosage is to use the uncooked version in Exhibit G and do this daily. It is wonderful. When the strong medicine slowly weakens and gets to a point where I need more medicine, it is extremely easy to re-balance. Just take a tablespoon or two or more for days of my favorite best method with hot milk in Exhibit G and I am rebalanced. I can just supplement the uncooked version. Continue as needed or just add a little of the favorite best method inside the uncooked versions. This is a food that needs a balance.

It is the NEW FOOD GROUP for Treating Illness!

You need to look at my food and the combination as a grouping of unique ingredients that can be interchanged. In Home economics in Junior High I was taught the old basic food groups. They are wrong combinations for this to work properly and heal illness as this patent describes. This is a NEW FOOD GROUP for treating illness. Quantities matter. Combinations matter. Potencies Matter and best of all SEED matters. This is the new food group. Each ingredient interacts with the other ingredients a certain way. You will find these quantities to work as a best method. The Best method for removing cancer and stopping the bleeding of gums and many other illnesses symptoms is the best methods in this patent and my favorite best methods. You can tailor down these best methods to basic Sesame seed/green tea/milk best methods and drink coffee with it. It is effective, but I demand that if you want to remove cancer or gain best results, use the other best methods. This is all you need to do. ABC Drug making, food style.

You will now see how cancer, diseases, mental illness, retardation symptoms and illness problems, illness, illness symptoms can be subdued with food. I have food combinations that do exactly this. You will have to say it is unique.

To My Sick Children Everywhere

You can make this as a Continual Drug. Just place ALL the ingredients in a large pot in the oven. Add all the milk (24 cups) in the Favorite Best Methods or Best Methods (Exhibit D and G) recipe at one time and just cook all of it at 350 degrees stirring constantly until dry instead of only cooking in 4 cups of milk at a time. (I prefer cooking 4 cups of milk until semi dry at a a time.) (Heck we could make this in a bread machine!) You never have to grind the seeds or powderize them. It looks like a Betty Crocker recipe. It is not. Then eat cups per day with hot milk and lower the food dose as instructed with oil. (ps. I ate this and lots of it, then quit taking it and 5 days later it is stronger in me than it ever was . . . . A Strong continual medicine. But, I still prefer the milk cooked at 4 cup interval medicine. The only cooked once version does not give me the all day strong anti-stress and narcotic benefit. It is just not quite good enough for me. I wouldn't use the uncooked version either. My illnesses require something strong. I need this drug stronger. I have a stress issue. Heating and cooking the ingredients all the way then repeating that action over and over again enhances this medication. Then have a couple of cups of coffee and eat my balanced food daily. It works. It is Unleavened bread with a sprinkle of cheese and a little green plant in it. This is Unleavened bread with green tea or java. The Jews I speak to say there is no milk in Unleavened Bread. I contend that The Israelites had goats and sheep and they made cakes out of that manna. Either way, this is UNIQUE and this patent is Expressly UNIQUE.

You are sick. You have no choice but to understand this. You just need to judge the food as a multi-illness symptom eradicator for the symptoms in Exhibit A. I will prove my illnesses are physical because I subdued many symptoms and stabilized my emotions and my mind with plain food mixed and processed. These are seed and seed derivative recipes that have virtually eliminated my mood and mind and pain disorder. (My pain can be almost completely removed or subdued. I just adjust the seed and caffeine. Too much seed causes sexual numbness but great pain reliever. I like a 2-3 tablespoon sesame seed measurement for enhanced sexual pleasure. 4 tablespoons cause the numbness to the point of decreased sexual sensitivity. I can easily increase sensitivity by decreasing the seed count, adding a glass of wine, and adjusting the green plant or seed.)

I am not ever going to tell you to take a medicine without a Dr.'s diagnosis. What I will tell you is these drugs are dangerous if you do them without a diagnosis. Would you take a mood stabilizer or an anti-depressant or a stroke medicine or a pain medicine without a diagnosis? I am not here to undermine a Dr. I am here to show you my list of symptoms. Look at my symptoms. Do you have any of these symptoms? I am not here to give you a diagnosis. My doctors got it so wrong that it could have killed me. I had stroke symptoms, blacking out visual impairments like I was being choked and the blood flow was stopped, and retardation and symptoms that look just like Parkinson's disease or Autism or severe ADD and doctor's never ever considered food could cure it. I had a severe mental illness that was physical and mental.

I ask you to use this Detoxification recipe as soon as you quit taking my best method or other recipe. Caffeine has to come out of your body and it is a nasty detoxification. I am telling you this because it can be easy or hard. A rice pellet will pound it out and if you really want to detoxify, eat 2 cups of cooked rice per day with little greens and a little milk and a little cheese. You need to do this many, many days (possibly a month) until you feel better. If you need a potent medicine, please use the sesame seed, green tea, and milk cooked recipes with this, but please only use a little. The goal is to get the food out of you. Caffeine and drug detoxification can be hard. I get headaches, body cramps, nausea, pimples and a just plain crummy feeling. Anytime I change recipes, I take large doses of the 1 best method at first to acclimate myself. I hate going from a strong green tea to a less strong green tea. Even though I am a coffee drinker, I refrain from too much coffee as it is hard to clean out the excess if you are pouring it back in. Oil must be added because this drug feels like a runaway freight train (feels like an overdose that won't stop) if you choose not to add it. This is a seed. It is always a seed. When you add milk, and caffeine you get a drug that should have oil to stop that issue. Eat 1 tsp of oil per day.

All the Recipes should be removed from your body when you quit taking these medicines. You must detoxify your cells. I do not want any of you getting out of balance. Use this above detoxification recipe.

Never assume this is just a food and just because it looks like Betty Crocker made it and missed the real benefits and actual recipes. It is very potent. I simply ingest them and it can takes days to get the full drug effect you need. This seed and this recipe will reprogram your cells, it will purge the bad foods and toxins out and it will make you emotionally and mentally stable within days. You may give people or children food. One issue is food is legal. Cooking is legal but making full scale drugs with seeds and seed derivatives and caffeine and milk and making it a potent "knock you on your butt" drug is not. We must now make this legal. The seed can be used as a food. The law says this is all cooking food. Possibly, two times or up to 6 times cooking it all the way (with increased caffeine and seeds) makes it a drug. Let us now look at the food as a drug. You cannot assume this is a food that does not have drug like qualities. Caffeine in chocolate can make these seeds so potent that a person or child can be affected. Caffeine is not needed. Caffeinated drinks can cause the same problems. I combine it for children and adults. I will make perfect potencies for all of us. PLEASE do not think these are simple food recipes. They are very potent and you now have a sample list of symptoms this food works on. It works on many symptoms and illnesses. I don't have a bad cholesterol issue. I can claim it removes bad cholesterol. The reason is seed helps to eliminate cholesterol problems. Therefore each ingredient contains it's already approved healing attributes. I can claim those healing attributes simply by using each ingredient for that healing attribute legally.

If you drink coffee or tea or another steady caffeine drink or you consume caffeine in quantities in any way this warning must be understood: You may need to decrease your caffeine drinking or consumption daily if you have a strong caffeine in your Best method. I cannot drink heavy amounts of coffee (or I get too imbalanced, too high, too off) if I use 3 tablespoons of sesame seeds or more and ¾ths tablespoons of green tea or more in my 1 best method or my favorite best method.) I have to only have 2 cups of coffee in the morning and maybe one at night. I get too "off" if I consume more. I just don't need it. The benefit to using this amount of caffeine is I almost always wake up almost perfect. With a less potent dose, it takes a few more cups of coffee to medicate me properly.

Warning: These medicines or foods look like just food. It will deceive you if you think it is just food. Every time I changed recipes and sample a new best method or simply start taking a new one, I must take the cups per day (especially when I add oils) then reduce it to get my mind and body acclimated. The warning is: For the entire time I am eating more than a tablespoon per day I am experiencing more than usual psychosis or the thoughts that this medicine does not work. It is a very hard time for me. The new food/medicine must have time to change you. It literally reprograms and changes your cells. You are literally removing the embodiments of one medicine or food that you have been eating (Like long named ingredients in your foods that you buy normally) and replacing the cells with a drug made from a mix of certain foods that creates a certain chemistry in your body. Imagine a strong hard rice pellet with green plants, a medicinal milk, a potent green tea and a powerful narcotic effect seed plummeting through your cells pushing out toxins, sedating you and then settling inside your cells at a certain wonderful mixture. Once the food or medicine is no longer in large quantities, you will find it wonderful. Many drugs on the market have this problem. It will be on the warning label of my new food medicines. So, the warning is "This will cause psychosis or pains or little irritations mentally until we get this best method in you as a normal operating medicine." Warning: I changed coffee. This greatly affected my drug. I was having an imbalance. I had gone to a discount store and bought bags of Columbian and bed and breakfast and since they both looked very strong, I mixed them. I was using ¼ cup in my coffee pot per pot. It is too strong. I am now using ½ to $¾^{th}$'s of $¼^{th}$ cup of that same mix to make a pot of coffee. It makes a difference when I use 3 not ground tablespoons of sesame seeds and 2 Tablespoons Stash green tea in my favorite best methods. I have to not have extremely strong caffeine since I am a coffee addict. Just make sure you can lower your caffeine intake. An addict has a coffee mug in hand. It causes an imbalance. I take the coffee pot (after my husband makes coffee) and dilute it by 50% with water. You should lower your daily dose of caffeine and regulate it. Use it as a tool 1. To help you increase potency and 2. Add milk to it to increase potency and 3. Don't drink too much or you get imbalances 4. To get you regulated on the existing medicine in your body like in the morning 1-2 cups of coffee make your medicine regulated.

This drug is a basic food. I have made a version of all the interchangeable recipes that works best for my personal illnesses. You will notice a unique characteristic: When you eat cups at first then reduce the dose to a tablespoon or more or less, you will notice the drug is stronger after you lower the dose as directed in the best methods. If the drug is too strong for you, lower the sesame seed and caffeine amounts in a 1 best method and start over with cups per day to purge the old medicine out and place in the new medicine or detoxify completely and start over with a lower dose of sesame seed and caffeine in your new 1 best method.

Although I have almost perfect focus on the 1 best method, I do not have perfect reading on the 1 best method. My focus is so perfect, it is hard to read fluidly. My other symptoms disappear or are greatly reduced by this combination (except for memory issues) on the #1 best method and many of the 2 ingredient (such as seaweed and lots of milk cooked) or 3 ingredients (such as sesame seed, lots of milk and caffeine cooked or seaweed, green tea, and lots of milk cooked) or less than 8 ingredient recipes (such as cooked fir bark water, milk, caffeine and evaporated milk). The absolute "most of the other benefits" far outweigh the slight problems I have in my typing or reading. I use this combination to live my life as a normal individual that allows me to live with very few side effects and as a best method for this patent pending. The problem with stating a best method is they all are great for multiple benefits.

This Patent is a Seed and it's Derivatives Processed to Provide the Claims Listed The Best methods are different for different illnesses, but you get many benefits with the best method that has a rice, sesame seed, milk, caffeine, cheese, green bean, oil, and a pharmaceutical drug or other herbs and medicines or classes of medicines added but not necessary.

The best methods and my favorite best methods are simply the ways I have made to heal the items in my Exhibit A.

I use the black or tan sesame seed as a potent medicine mixed with the other seed to maximize the benefits of my medicines. I do not ever want to get high. Too much caffeine or too much of seeds with a narcotic effect harm the ability to function naturally. I have found this mix to work best for my illnesses.

but I have made a cracker or a bread that can be sold daily to the entire world and this is it, my best methods.

There are Different Combinations You Need to Focus on

1 Processed seed and Milk and caffeine (Caffeine is not needed, but is a best method) Look in Best methods to find a recipe for this.
2 Processed Green Plant, Milk and caffeine (Caffeine is not needed, but is a best method) Look in Best Methods for this.
3 Processed Seed, Sesame seed, green tea, Milk, Cheese, green plant, oil, Look in Best Methods for this and Diane's favorite Best Methods (cooked and Uncooked versions) Meat can be added. Fruit or wine or alcohol can be added.
4 Pharmaceutical Drug or Processed Drug, and the #1-#3 combinations.
5 The ingredients inside you processed at 98.6 degrees avg. (You can use animal temps also.)
6 Unprocessed Seed, Seed Derivatives, milk, green tea
7 Unprocessed Seed, seed Derivative, milk
8 Unprocessed Ingredients
9 Combined Ingredients
10 How these continue inside the human and animal body
11 How and what to eat to maximize potency
12 Processed Ingredients All these ingredients can be interchanged, but to make a myriad of different drugs, try interchanging the sesame seed for poppy seeds or fennel seeds or Evening Primrose seeds. Try exchanging the green beans for seaweed or broccoli or other greens. Try adding different Pharmaceutical drugs or other drugs or herbs into this basic mixture and come up with many new drugs. Just mix them in and make them continue. How hard can that be? Just add oil. They just need to be added into this patent. There are so many variations that I cannot even begin to tell you all of them. You just need to know that these basic best methods will do so many different healings. Each ingredient is packed with different benefits and by using the benefits of an added ingredient or drug, you have virtually eliminated almost every disease on this planet. The seed can be interchanged with like kind seeds. The Green plants can be interchanged for other greens. I can interchange cheese, sour cream, milk and want you to try the same. I have even used sperm and vaginal juice and saliva. It causes a wonderful potency with evaporated milk. I have many incredible variations. I have been doing this successfully for 5½ years. Many combinations work.

Take the above combinations to concentrate on (listed above) and use these as your testing template. You will find a myriad of drug combinations. Interchange the ingredients and see different combinations with interchangeable ingredients. Use like kind ingredients as an interchangeable template: Many recipes are best methods and each ingredient or recipe has its own benefits and characteristics and you can change the drug by adding a seed or seed derivative, plant or herb or add another drug that has specific unique benefits and characteristics.

Explanation: 12 sheets of seaweed sushi squares cooked in 1 gallon of milk until dry. Eat with hot milk. To make it more potent Take the same recipe and cook 2 green tea bags in water until water is dark. Remove the tea bags and cook those seaweed sheets with the green tea water and milk. Both recipes work. One is a lot different food than the other. I consider both of these simple but not my best methods. These don't have a long term drug effect. I made a over 21 day narcotic. It just kept on strong for 21 days. The best method for a long term drug effect has seed or rice in it. Oil makes this long term medicine able to medicate long term. You have to discern what you want from this drug. Do you want long term or short term medicine? I consume both with hot milk. I love many of the basic combinations and combining different ingredients with milk and green tea allows me to sample many wonderful mixes of best methods. I can combine any of these and make a myriad of different DRUGS.

Seeds that are just placed in the recipe. Grinding seeds is not needed, but increases potency. It is not needed. I made my favorite recipe with not ground sesame seeds for years and then one day I ground them. Seeds expand and can cause narcotics to be very strong. I add greens, milk, and an activator so they are in a very potent environment. Please drink oil or add oil to make it continue with a great continual drug. Let me show you how to reduce potency. Please just use a smaller dose in your recipe of small dark, brown or black seeds. You can see potency clearly after 10-30 days of use. To lower a strength example: do not use 4 Tablespoons of Black sesame seeds. Use just 2 . . . (or 3 or 2.) If You are not taking any of this medicine and have already placed the continuation drug in your body and are eating only food to maintain a good and perfect balance, please understand that too much of a green causes the narcotic to move out, too much of a grain will do the same. Too much of an oil can cause increased narcotic effects, too much green tea or caffeine will cause an increased medication effect or imbalance, too much of a small seed cooked in caffeine and milk many times will cause increased medication drug effects, too much of cheese cause a wrong psychotic effect and too much wine will cause a detoxification. Keep the balance of foods as listed in best methods and just eat a little every day. Drink coffee or green tea first thing every morning to get the medicine moving fluidly through your body. It immediately removes any psychosis or issues you may have first thing in the morning. Drink a little oil to stop your imbalance and always re-regulate with the best methods listed. You don't even need to make this food with green tea, coffee or caffeine. You could just cook the oatmeal or sesame seeds or green seaweed with milk many times.

I take 1-2 Tablespoons with hot milk per day (always take much 1 cup to 1½ cups at first and lower amounts until acclimated).

YOU MAY DRINK ALCOHOL with this and enhance the medicine and cook it directly into this. You must put a warning label on these drugs that states that alcohol will increase the effects. Alcohol can be added to many of my foods or medicines listed in this patent. You do not need to drink alcohol if on this. I only need 1 glass of wine vs a bottle to enjoy wine. This medicine is so wonderful and I feel absolutely great all the time, I do feel a need to drink. It will decrease the need for alcohol. An alcoholic would not need to drink if on this. Your moods, body and mind are stabilized.

Overdoses can continually occur when fermentation or seed is inside this patent. Be Careful. Overdoses can repeatedly and continually occur every day when a person stops using this medicine unless oils are added or detoxifying is with recipe that includes cooked rice, greens, and milk or grains or seeds and continual use (or use my detoxification methods in this patent . . . grains, milk, cheese, greens, etc. Greens will help.)

Please note that these ingredients are interchangeable with other ingredients and thus making this patent expressly-unique. I am making many interchangeable parts of or interchangeable seeds, flowers, plants or trees or shrubs, milk, substitutes, milk derivatives, sperm (seed), insect bodily fluids, bodily fluids, or other ingredients and drugs that stops anyone from copying this. Use fermented milks, add ferment or fermentation, cheeses and grains, seeds, and fermented grapes, or alcohol, wines, or other additives, sand, green plants or black plants, trees, shrubs, parts thereof and many other ingredients or parts of any listed or substituted ingredients processed in many ways. Many processes can be used to make these ingredients and drugs.

This will appear to be normal food. Be very careful in judging this recipe.

I need to warn you: I have tried many seeds (fennel, poppy, evening primrose, sesame, and different seeds such as grains, rice, wheat) and I do not love all of them. Each has different characteristics and benefits and I have blended certain seed to make this patent work and many variations are possible. I do not pretend to know all the seeds or plants or combinations, but I have proven that the ingredients are interchangeable and many can be used. The world is filled with seed and we should use them. You will find each seed able to be utilized. You will not love all of them but will find that seed will work. Each ingredient has unique characteristics and benefits that will change the medicine. These ingredients can all be swapped for like kind ingredients. Example: Milk is from the human or animal body and is interchangeable with sperm, human or animal fluids or body parts such as meat, cheeses, eggs, fluids from the body, mayonnaise, evaporated milk, other milk ingredients and wines.) Green beans and Seaweed, and even pistachios are both interchangeable, but both have extremely different characteristics. I also can interchange the exact seed, such as sesame seeds for fennel seeds or poppy seeds or other seeds. I even can substitute cheeses for wine. Milk is the best for just about all of the recipes. I interchanged it with evaporated milk, cream, sour cream, eggs and sperm. I still found milk to be the easiest and my favorite. A child in the desert with no medicine can probably find a goat and milk it and pull down some seeds and pick up some green plants to make these recipes. There are just way too many ways to substitute items, ingredients or dissimilar or similar ingredients and come up with a very good and unique patent. Some seeds and plants and milk or wines are much better and it is obvious that if you use better ingredients, you will get a better end result. These ingredients can all be made more potent. Use more potent ones or just use the basic ones you find and they work no matter what. Ingredients have unique benefits and ingredients can be better than others and all are made to produce its own unique benefits and problems. Do not assume all seeds or ingredients, or parts thereof, are equal. The world is filled with seed. I have satisfied the uniqueness of the patent by proving that many seeds and other ingredients, or parts thereof, can be used. You need to also know that every green plant and seed and bark and many other ingredients that I used with green tea and milk in the desired potencies also was effective. You must know that I can even add this to a human body and form a continual medicine and therefore have proven that I can place this inside a continuum (example: the human body) and make it function continually. This proves I can make a continuum work with this exact patent. This, patent is a Continuation Food. This food is a continuation food and when combined a certain way as described in this patent, it continues with the same claims and benefits many days thereafter. This is also a Continuation Drug. (I took the 1 best method for a month or two and drank cups of The processed Evening primrose oil and then stopped taking the drug and oil. It stayed in me as a continual drug for 21 days. This drug is a continuation drug and when combined a certain way as described in this patent, it continues with the same claims and benefits many days thereafter. The FDA has already approved drugs for consumption with food. It is still food.

Please note that a continuum can be any machinery that has an engine or a method of movement. A Continuum is a place of continual (like an engine or a blood flowing with a continual heart or a continual blood movement) flow. I can place all the ingredients combined into a long skinny tube that is circular and connected and blow air or more ingredients into this tube and create a continuum that is a machine. I can add blood and a heart or a machine that pumps. The ingredients in this continuum make this patent move continually and thus can accomplish anything that the ingredients or the combination of parts thereof or its effects on the continuum or it's ingredients inside can produce by many combinations of ingredients or combined effects and results of these ingredients. I did notice that some seeds were much better than others and am using a sesame seed only as my favorite.

Continual Drug Inside a Continuum

Medicines are Food but make you well. The patent's ingredients and combinations of ingredients will combine with medicines already on the market, thus eliminating the need to buy some Pharmaceutical drugs. You can also see that if people don't need to buy other medicines, I will be able to decrease the cost of health care. Please examine what a continual medicine in the drug market would do. (You can also demand that if I choose, I can simply drop a persons need for their current and in-use medicines to a fraction of what they are buying when consumed or mixed in cooking with my medicines.) The food that continues in the human and animal body is inside a continuum that keeps this medicine repeatedly moving through the human body. The human and animal body is a continuum and can be replicated in another environment. These medicines have been used on me and my cat. (I had a highly active, extremely jumpy, can't seem to ever sit still, very busy cat who pulled out the scrapings from my baking dish (a large quantity) and ate it and loved it.) This can be used in Pet Food. This food can be added to the continuum or just not used. I can continually eat this food and thus continue it and I cannot eat this and continue it. I can also add a Pharmaceutical Zyprexa to my favorite 1 best method for a few months and then just eat the uncooked version and make the drug last a long time. That reduces the cost of any Zyprexa on the market. The medicinal benefits continue. I can add medicines like Zyprexa or other medicines and this will lower the dose of Zyprexa and make this medicine continue. I can add other medicines like Lithium and this will lower the dose of Lithium and make this medicine continue. Overdoses were all eliminated by adding oil into these drugs. I can take 4 Ibuprofen and it semi-knocks me out so I can't wake up in the morning. Sometimes, one glass of wine is too much for me. I used to drink 3 glasses. I cannot handle any more. I only need 1 glass. I can add a glass of wine and make this medicine an interchangeable other drug or food.

I have used all of the ingredients listed. These all are used for the claims. Please know that these are continual medicines and are very good if you take them and make sure your body is filled with these before you ever stop or halt using them.

This drug is to be used by all people who hate going to the Pharmaceutical companies or going to doctors who have a great problem in diagnosing our illnesses. It is for the people to judge. I am very ill. When I get sick, it is imperative to make myself a large dose of this recipe and take a large dose for many days. It causes a mild psychosis in me during this phase. I have to endure that to get to the right dose. I always lower the dose to my needs, but only after I have flooded my body with enough of the medicine to create this continuum.

Each ingredient and each combination of ingredients has its own inherent benefits. Each ingredient and each combination of ingredients has its own healing abilities. Such as Milk with Vitamin D in it has all the benefits milk has. All the characteristics and benefits of each of my substituted ingredients or ingredients have the inherent characteristics and benefits and abilities of that ingredient or combination of ingredients.

Seeds, seed derivatives, Grains, minerals, vitamins, green plants, black plants, minerals and vitamins, trees, flowers, fruits, shrubs, teas, coffee, seeds, milk, fermented ingredients, oils, meats and most foods change this recipe and add to it to provide all the claims provided. I interchange all of them and get different results based on the illness or disease. It is not difficult to heal all diseases. I just change a few ingredients and process it by either heating, cooling, grinding, blending, and several other processes by combining these exact listed claims and ingredients and parts of and a process of digestion and these basic processes are all I need to heal the animal or human body.

Mix with a strong SEED, SEED DERIVATIVES, GREEN PLANT, TEA and MILK DRUG and you are able to fulfill the listed claims. The basic mix is seed, green tea, green beans, rice, wine, cheese, oil, milk, and meat. It is a wonderful combination. Each ingredient is used to help with the issues and illnesses and problems I have. Imagine all of it 100% replaceable with a different seed, a different oil, a different green plant, a different milk or sperm, a different tea or coffee, a different grain or flour or rice, a different seed, a different meat, a different cheese or wine or alcohol or fermented ingredient or fermentation that speeds this process up or any different ingredient that has already been patented and any other medicine, patent or available drug. I can add many drugs or medicines, or herbs, or plants or patents or many other medicinal ingredients or combinations thereof. You can do the same. It is easy.

Use quantities that eliminate the issues or problems. I have used these ingredients in wrong quantities, types of ingredients, in improper ways, combinations and it caused psychosis or overdose. One wrong quantity harms the recipe. Always remove the patients excess food for a detoxification in their body by placing normal exact quantities of a basic uncooked or mildly cooked form of the grains, greens and milk into the patient's body and removing the green tea and sesame seeds or small dark seeds can help and will push out excess.

I eat green beans for dinner sometimes or a glass of green juice and it causes an imbalance in me and a detoxification and I then need another dose of the medicine to stabilize me or a cup of coffee. It is like detoxifying off of a drug with mild shaking, body aches and stress and whatever the medicine was doing for me seems like it becomes almost non-existent.)

Increasing potency is a unique process and can be done many ways such as in an oven, in a microwave, on a stove, with fertilizer, in the ground or in a blender, agitating it, cooking it longer, in a cooling area, by grinding or other method of increasing potencies of seeds and seed derivatives the seeds and in increasing potencies of all seeds and plants and trees and shrubs and flowers and processes or just placing the ingredients in the patent. The human or animal body mixes, and combines and processes the ingredients. The natural 98.6 degrees is processing these foods. The best method is just to find a normal regular dose that can be maintained daily.

Patent process . . . : You can even just cook or eat uncooked ingredients separately and the combination of these ingredients can cook and combine inside the human or animal body and cause a drug effect.

This method is best as a food or a drug. This is only one of my incredible ways to process. Most people assume heating, cooling and mixing are processes. Processes are anything that produces the food or this patents claims and all the derivatives, sub claims and all the derivatives or this provisional patents or these exact ingredients or these patentable ingredients and their combinations ability to do exactly what I provisionally filed in this patent application. Processes are also combinations mixed and heated or cooled and thus it changes the foods core ability. These ingredients are used in certain temperatures, processes and amounts to prove the patent claims.

The best method to simply make strong drugs is to use a seed. The best method to make a seed continue is to add the basic ingredients Listed in the best method. The best method for great non-narcotic medicines is to use greens, (with or without) green tea and milk combinations. You will enhance sex on Best Method 1 and it even better with one glass of red wine added and good relaxing music. The drawback is a numbing from the food. To enhance the feeling, lower the seed and caffeine in the food combination. The best method is to use oil in your recipe. The best method for pain issues and other illness issues listed in my claims is to use seeds and green tea and milk combinations. The best method for removing seed formulas is to eat the detoxify foods (and massive greens if you need a quick detoxification) listed in this patent.

You can interchange different drugs in this patent. I cooked in Aspirin, and Zyprexa and Zydis. You may combine this patent with anti-psychosis medicines with that specific benefit as an example Zyprexa in my combined adaptable food medicine. I used aspirin, Zyprexa, lithium and many can be added thus making it interchangeable. You don't even need Pharmaceutical drug to combine with my patent'. You can simply just eat it as food.

You do not need-green tea. Black tea works also. Substitute for caffeine drinks or food on the market or substitute caffeine. Coffee is used to enhance this food. Drink it and it helps the food. Milk works by itself. Seed works by itself. Ingredients work by themselves. It is best to combine them for the desired healing. It is best to cook them. Plain Greens in milk cooked as listed works. Plain seeds in Milk cooked as listed works. Green tea cooked with these ingredients makes it strong. Evening Primrose Seeds (inside seed is the oil I processed to cure my lymph node cancer and other ingredients)+ Milk+Green Tea (or you can add greens) heated as a anti-cancer and anti-malignancy drug) as an example. Use much processed Evening primrose Oil or plant for cancer patients or just use it regularly. Ingredients and parts of or insides of ingredients are Interchangeable with other ingredients or combinations of ingredients, and earth ingredients above or below ground.

Ingredients include any part of an ingredient and are not only interchangeable but you can add more or less ingredients to this formula. Attention Deficit Disorder symptoms can be alleviated with just seed, milk and a little cheese. It is preferable to use the best methods.

The temperature and the actual human or animal body mixes, and combines and processes the ingredients, combinations, and parts of each ingredient. I can take each (maximized potency) ingredient and eat them separately and my body will mix them and it will work, although it is not the method I prefer. (My favorite way is to cook it then eat it, but it is not necessary.) Cooking it makes a better potency.

The interchangeable ingredients can be added to many: ingredients, patents, drugs, medications, minerals, vitamins, food, non-food, herbs, rocks, volcanic ash (I cooked sand and dirt into these recipes), and other combinations of other ingredients. You can add ingredients or subtract ingredients.

These ingredients can be processed in many ways or eaten as food. These processes and heating of can increase potency. These ingredients are used in certain temperatures, processes and amounts to prove the patent claims.

Ingredients can be raw or processed in many ways.

This can be used as a food, a drug, a continual drug or narcotic or as an example a 21 day narcotic and a continual herb or a continual food or a continual drug.

It is now proven that a continuum can hold continuing interchangeable ingredients and continually move and create the same effect and this is proof that I can make all these ingredients continue. This is continuing medicine, food, or drugs, or energy. Please note this patent is Interchangeable. Please note quantities are important and should be used as described (but not necessary).

Replace green beans with green plants. I have used, spinach, turnip greens, broccoli, green grass, pistachios, and my favorite seaweed.

Replace seeds with seeds, grains of many flours, coffee beans, wheat, fennel seeds, poppy seeds, primrose seeds, green tea seeds, rice and grains, and Life cereal.

Replace milk with cheeses, goat cheese, sour cream, eggs, sperms, bodily fluids, animal fluids or ingredients, human fluids or ingredients, mayonnaise, evaporated milk and fermented ingredients. Once this is placed inside the human or animal body, it mixes with the other human or animal body fluids and parts and thus is part of this patent!

Replace cheese with wine, fermented ingredients, alcoholic ingredients, beverages and plants that ferment. You do not need to do this.

Replace green tea leafs with Black tea leafs, green plants, cocoa, coffee, other plants, tree parts, trees, shrub parts, shrubs, plants above ground and below ground, minerals, rocks above or below ground. Ingredients can be added to or subtracted from, processed or unprocessed.

Replace Olive Oil with Primrose oil or Sesame seed oil or seed with oil in it or other oil. It is easy to use an oil and easier to not use one.

Replace seed with oatmeal or grains or seeds that have certain healing ingredients or properties or roots, or flowers or seedpods or parts of plants, shrubs, trees or above earth or below earth ingredients. Try adding Valerian Root or the plant. It makes a wonderful drug. Herbs all have healing abilities that can be added. Get a list of all the healing properties of herbs and plants and roots, etc and just add them into this patent and create a new variation. I already added this into my claims. You can actually add minerals and vitamins and many other medicines and herbs and make very distinct medicines with unique patent claims in each.

Narcotic effects are noticeable if you use too much of a seed, hallucinations, colors, lighting are examples. I have never had any habitual need for these medicines (except for my coffee habit that I have had for 30 years.) It is easy to get off the food. DETOXIFICATION: Simply eat the same ingredients as a food and do not add sesame seed cooked in green tea or just use a low dose of seed cooked in tea/milk with the same ingredients uncooked (cook the rice). Detoxify patients with these ingredients daily (or use doses of unleavened grains with no yeast.)

I had yeast infections 3 times after trying to get off this continual medicine. After I took the generic or regular Monistat, I noticed it still felt like it was in my vagina and anus. It was strong and very uncomfortable. I had forgotten to eat the balanced foods like I needed to after I quit the basic methods. I immediately ate a large bowl of rice, covered in milk, and ⅔rds cup of green beans and had a cup of coffee. It greatly enhanced this drug. It made it last and made it very strong. It also eliminated the yeast issue. The best way to reduce the drug effect and eliminate the yeast issues that I had is to continually eat these same ingredients in Best method exhibits in uncooked or slightly cooked versions and the best method to increase potency is to eat meat, drink coffee and eat a bowl of rice, greens and drink milk.

Oil will stabilize the medicine but causes intoxication. Oils make this continuation drug operate properly. Processed Oils can be used as an anti-cancer drug or food. I use either Olive oil, Safflower Oil or Evening Primrose oils and Wesson Oil. I will take oil with the initial 5 days of medicine and then stop and the oil has made this a continual medicine where I do not need to take a daily dose.

The reason oil must be utilized in this medicine is you will have severe issues if you do not add oil. Let me explain. I ate the 1 best method for weeks and used 2 tablespoons of sesame seeds and $¾^{th}$ tablespoon of green tea in that best method and greens. My body had been fully saturated with this medicine and I had successfully lowered it to the medicine to about 1 tablespoon per day. (Then no drug eaten at all.) I had not added the 1 tsp of oil into my daily medicine. I chose to eat it only with the tiny bit of oil that was in the recipe. I noticed that during the day, it would build up in me like an out of control freight train feeling. This is an overdose. It can easily be stopped. I went to the kitchen and drank 4 tablespoons to 1 cup of Safflower Oil. I kept eating 2-4 tablespoons of this oil per day. It took about 5 days, but the overdose-feeling slowed. I continued the oil. A best method is to add oil. You can do it many ways. PUT OIL IN YOU. A way to reregulate you is to purge out the old and replace with the new. You also should start over and retake the 1 best method and eat the oil daily with the new best method. Do not skip oil. Oil must be in this recipe. It is a continuation medicine. It continues. The oil eliminates this problem. I also slowed down on my coffee drinking. This is important and simply is required. Now, I just add 1 tsp to 1 tablespoon of oil to my 1 best method daily dose per day.

Another reason is that when you quit using this medicine you should eat the same ingredients or their interchangeability substitutes to help with their balance. I quit using my best methods 3 times and got yeast infections. The more meat I ate, the more it seemed a problem. I was not eating these ingredients after I quit taking my best methods. The meat was purging out the medicines in my body at a fast rate. The problem was, the yeast. So, I immediately started eating a ½ cup or more of rice, a tsp to a tablespoon of greens, milk, and oil is also needed and started purging my body the right way. This is needed. You body has been filed with this medicine and it can detoxify yeast. You just need to eat these balanced interchangeable ingredients to balance your mind and body if you use this as a continuation drug or a food.

Best Way to Add Oils: The 1 Best Method

Another Best Method:

When I use Cooked Evening Primrose Oils at extreme temperatures (you can place it in the freezer after each high temperature heating) and add it to daily above foods. This is how: Treat yourself every day with high doses of a Primrose oil or plant 4-10 time heating at extreme temperatures and (cooling after each time). I added greens to help it move through the bloodstream and added a analgesic to alleviate the psychosis and body pains associated with the processed Evening Primrose oils (primrose oils are fine). I needed the narcotic effects or the analgesics to remove the pain (and it burning out my cancer) associated with the oils in my body. I noticed how when I looked at my skin, it looked like I had been burned from the inside. I then maintained a regular dose for 6 months. I treated myself intensively a few times. I continued these treatments on and off for 1½ years. I also did an intensive treatment 2+ years after my cancelled surgery. It burned. I could feel it. It caused mild, continual irritating (severe enough to need a calming and pain reliever) psychosis that I used my (Fir Bark brewed in water until dark and only use the fir bark water). Freeze the bark water and cook it again. Repeat this 3-10 times. Then take 1 cup of dark 3× cooked and frozen Fir bark water and mix it with 1 cup of milk to 2 cups of milk and cook until dry. Consume. Notice that I did not use tea here in my recipe. You can use it or not. When I processed the oil at a 10 time cooked and freezer overnight process and used it in a normal manner on a skin issue, it burned a blister on my skin when I covered it with a Band-Aid and tried to eliminate oxygen. You and I are no different. The only issue is "are you able to handle a drug burning inside you?" I did. I had no choice. It wasn't that bad. I still had my hair. I had to heal myself and my cells. It is a healing medicine. I had no hair loss, no deadly chemical burning in my body and no other cancer has popped up in 4 full years. I had Lymph node cancer. The original 1½-2 inch fast growing tumor was NOT the primary origin or the place of origination. The doctor said it was in my cells and it was a fast growing cancer. He said it was secondary and there was no way to find the primary source. The Dr. told me when I walked away and cancelled my scheduled second surgery, and his demanding of chemotherapy and radiation that it would more than probably be back in because it was a 3 month fast growing tumor that was originally taken out and would be fast coming back. He said within less than 1 year and 2 maximum and it would then be probably too late. He wanted me in surgery, chemotherapy and radiation. I told him NO. He then agreed to every 2 month invasive checkups. I agreed because he pressured me, but I never went back. I burned it out of myself. It and other recipes removed my cancer. I combined my Evening primrose foods years ago with a bark narcotic (Fir bark boiled in water a long time until very dark and condensed and then placed in freezer. I processed the Fir bark water 3 times like this. It can be processed many more ways and times and easy ways such as using the actual bark and not just the water. I froze it. I then used a little daily for my illnesses. It is a great medicine and was my first major medicine that worked on many of my symptoms and illnesses. Take 1 cup to 1 Tablespoon of the Fir bark water and mix it with 1 cup of milk to 1 Tablespoon of milk and heated it until dry. I then added the Fir bark milk to 1-5 Tablespoons of activated or heated processed 4 times Primrose oils and consumed it and other interchangeable ingredients and then lowered the dose of oil to 1 tsp per day daily plus interchangeable ingredients for 1½ years off and on. This is how I eliminated my cancer. I burned it out of me. I continually take the best methods. Tree bark just comes from a seed originally. Bark is interchangeable with seeds. The use of seed and its derivatives was used at all times.

Evening Primrose plants are food and so is Evening Primrose oil.

Continual Food, drugs and any addition with extreme caffeine activation makes this bread and the fermentation created an overdose continually in me. My stupid problem was I placed mold into this medicine and tested it. I did not know vaccines were a placement of a virus into a vaccine. I was on a mold that had taken over my body. It was not a vaccine. It is a continuum with an out of control mold continuing. I almost died. I purged myself of this mold with my best method.

This is how to make this food continue: When starting your daily doses, simply add oil. I add the same amount as the dose for 6 days, (and I eat a bowl of plain oatmeal to help with nausea from consuming oil) then I simply stop taking any of it or simply the food medicine without the oil. You will notice that this medicine will continue in your body. Oil is needed to continue. If no oil is used, you could overdose. Oil stabilizes the food from imploding in the body.

This patent is cooked, uncooked, oxidized, fermented or many other ways to process. Seed is the starting of the plants, trees or shrubs or other items to make this patent. I used all parts of plants. Oil comes from seeds or from plants. Take the Evening Primrose Oil and cook it at extreme temperatures and freeze (hours at freezing temperatures) and repeat this as many times as necessary. I did it 4 times. I used this 4× Evening Primrose oils and burned out cancer. It burns. Daily, I activated the Evening primrose Oil by heat and consumed it. I cooked it and consumed it many ways. This was my favorite way.

My Cancer Personal Daily or Needed Doses of this Medicine are:

A continual dosage of The Evening Primrose Oil cooked at high temperatures, then placed in the freezer 4 time for both at a high initial dose and a continual dose for about 1½ years. I then treated myself intensely a few other times and I continually have used these medicines for 4.25 years non-stop. I take basic milk and Bark water and all 1 tsp of a 4 times cooked and cooled version of the Evening primrose oil and used it daily (with many other variations but with these 3 ingredients being consistent) for many months. I also interchanged the bark for other Ingredients and always had milk in the mixture. I used milk as a basic ingredient for 4.25 years. I chose to keep a steady dose of a grain and an oil and a green in the exact anti-cancer removal of my cancer. It was never just the Cooked and processed Evening Primrose oil. It needs to move through the body. Greens will do that. Grains will help and greens and grains will eliminate it from your body. I cannot allow you ever to make this look like just an oil doing the job. It is a removal and healing and cellular rebuking food. The people who claim to know medicine will understand it. The process of rebuking viruses, malignant cells and toxins.

Consume 1 Cup of 4× Evening primrose Oil and add 1 cup of the 1 Best Method Recipe.

Then repeat this 2-days. Then 3 days of ¾$^{th}$ cup of each.

Then use 2-4 Tablespoons of Each. Then lower to 2 Tablespoons of each. Then lower to 1-1½ Tablespoons of each then lower it to 1-3 tsps of each. Then stop using any of it and it will cause a continuation. (redo this as needed). It can also be made better by allowing low doses of the basic recipe daily. Then start taking 1 tablespoon of the 1 best method for a season with Processed evening primrose oil.

Use the Favorite Best Method and the 1 Best Method to continually treat Cancer.

Rocks (Sand), soil, dirt, and other rock ingredients (Volcanic ash), land substances, and the contents of these ingredients and earth ingredients or parts of the earth benefit this patent. I have used them all. Use the minerals and what's in these ingredients to add benefits and change the Patent into a different function and inside these ingredients the results will be the additional uses to make this patent and many others. To make these items easily digestible, I cooked sand, dirt, rock, volcanic ash and added it.

The rocks all have different functions. Each rock has many qualities and benefits.

You can change the benefit with exact rock benefits.

These are some of the patent medicines samples:

Green leaf, milk, green tea and interchangeable ingredients cooked.

Seed, seed derivatives, green plants, shrubs, flowers, milk, green tea and interchangeable ingredients cooked.

Seed, Green tea and milk and interchangeable ingredients cooked.

Tea and milk and interchangeable ingredients cooked.

Tree parts and milk and interchangeable ingredients cooked.

Plant and milk and interchangeable ingredients cooked.

Seed of animal and man and milk and interchangeable ingredients cooked.

Grain and wine, seeds, seed and seed derivatives, plants and interchangeable ingredients cooked.

Seed, Seed Derivatives, Grain, wine, oil, milk, plants and interchangeable ingredients cooked.

Grain, wine, milk, seed, oil, plants, and interchangeable ingredients Cooked.

Each ingredient has its own individual healing. Example: all the benefits of milk in this patent are inherent in this interchangeable seed patent. The exact characteristics of an ingredient and the exact ways that individual ingredient is with other individual ingredients are part of this patent are inherent in the ingredient and are a distinct patent right.

I made a seed and it's other ingredients continue in the body. I used no cancer or virus to vaccinate anyone.

Recommended: If you take any of these recipes, including best methods, that continue in the body, it is a best method to eat a balanced diet or detoxify with one of the detoxification methods. The best method is daily: a lot of rice, a little cheese, greens, and milk. It is not a hard concept. If you place a continuing drug in you and you need to get rid of it, take these and detoxify.

Many ingredients and interchanged ingredients in Exhibit F. You may also get a list of all the healing properties of herbs and plants and roots, etc and just add them into this patent and create a new variation. Explanation: Exhibit F is an example of many different ones. Every sampled worked. There are too many different seeds and seed derivatives on this planet. You should sample all of them. This patent claims that I am only providing a small sample and many different ones can be used. Each ingredient is inherently different.

Add milk with seeds or seed derivatives or, plants and agitate it, blend it, cook it and you will make a stronger, more potent food.

<example is 12 sheets of Green Seaweed for sushi squares and 1 gallon of milk. Place in blender and blend until an even color. Cook it until dry. Another example is instead of using Seaweed, use $1/4^{th}$ to $1/2$ container of Spice Islands Sesame seeds (or Dark Brown Fir Bark water) instead of Green seaweed. Add the gallon of milk and cook until dry. Consume with hot milk>

Add caffeine and milk with seeds or seed derivatives or plants then agitate it, blend it, cook it and you will make a stronger, more potent food.

<example is 12 sheets of Green Seaweed for sushi squares. Cook 2 tablespoons of green tea in 3 cups of water. Cook the tea until the water is dark. Use only the green tea water and discard the tea. Combine the green seaweed and the gallon of milk and the green tea water and blend it until an even color. Cook it until dry. Consume with hot milk. Now, instead of using Seaweed, use $1/4^{th}$ to $1/2$ container of Spice Islands Black sesame seeds (or Dark Brown Fir Bark water) instead of Green seaweed. Add the green tea water and the milk and cook until dry. Consume with hot milk.> The ingredients in this patent are used as a fuel source to make energy. <example: Food ingredients are used for energy in the human body. Food can be converted into energy.

Example: Ethanol.>

By using Pharmaceutical prescription drugs or non-prescription drugs or ingredients or other combinations of ingredients in this medicine and processing it, the Pharmaceutical drug or non-pharmaceutical drug or added ingredients last much longer than it would by itself and you will need a far less quantity to get the same effects. <This drug is an easy way to use much less of the Pharmaceutical drugs and other medicines, and other patents than they would use to get the same benefits when added to this patent. One example of how to do this is: Once you normalize the person, simply stop taking it and it will continue. Another example is just add small amounts into your best methods. Another example is just add small amounts of the above medicines as this drug continuous in you to maintain your medicinal needs. (Then you do not need the excessive drugs in your medicine as the benefits will 1. continue or another way is 2. Lower the amount in the best methods or 3. Make it a Continual medicine and just add small amounts to maintain the dosage thus lowering the cost of Pharmaceutical drugs.) This patent has the ability to make Drugs less expensive will make my drugs more appealing to the people. (The Dr's had me on $800 per month mood stabilizers.)>

It is a New Interchangeable FOOD Combination for Illness Treatment. <Example: You need to look at my food and the combination and quantities as a grouping of unique ingredients that can be interchanged. This is a way to treat illness. In Home economics in Junior High I was taught the old basic food groups. They are wrong combinations. This is a NEW FOOD GROUP. Quantities matter. Combinations matter. Potencies matter and best of all SEED matters. This is the new food group. Each ingredient interacts with the other ingredients a certain way. You will find these quantities to work as a best method.

This patent rebukes cancer, cancer cells, and kills cancer. You need to burn it out and then let it burn inside at a normal human body heat with a certain mix of ingredients that remove the cancer. This process is continual. These medicines have an oil and milk. Another way is to continually use the best methods to remove cancer cells.>

You can interchange ingredients. An example is copy seed for seed and the plant based seeds or plants for plants, and green plant for plants, tea for coffee or other substitutes, cheese for ripe fruit, and cheese for wine and oil for oil and caffeine does not need to be added.

A small adjustment in ingredients changes the medicine. <Explanation: 2 examples are 1. A small adjustment in Sesame seed or its interchangeable ingredients changes the drug. 2. A small change in caffeine or its interchangeable ingredients changes the drug. 3 Tablespoons of Sesame seeds and 1¾$^{th}$'s tablespoons to 2 tablespoons of Green tea is a much stronger drug than 2 tablespoons of sesame seeds and ¾$^{th}$ tablespoon of green tea. (Testing this in the 1 best method shows this.) I do not like strong medicines that do not allow me normal day-to-day energy and enthusiasm. The higher doses of these above ingredients cause me to not to operate at my normal energy level. I prefer the lower doses. If the dose is too low (not enough caffeine or sesame seed) the medicine is not strong enough for me. (An example for a too low dose for me is 1 tablespoon or less of sesame seeds and less than ½ green tea bag or none used in 1 best method). I prefer the higher doses for acute issues and acute pain.)

The ingredients in this patent can be used as detoxification. <The ingredients in this patent, seed, milk, rice, grains, greens, cheese, and its' substitutes can be used as a detoxification. Explanation: When I use a 1 best method that has 3 Tablespoons of sesame seeds and 1½ Tablespoons of Green tea in it and I use it as directed, It is difficult to detoxify. I must either use full recipe doses of a 1 best method with 2 Tablespoons (Or less) of sesame seeds and ¾ths tablespoon (or less) of green tea in my 1 best method recipe and take large initial daily doses to move out the old recipe or THE BEST METHOD: Eat 2 cups (to 1 cup) of cooked rice with 2 tsps of green beans, 1 tsp of aged cheese and 12 ounces of hot milk every day until the old medicine has been removed. The latter can cause Detoxification symptoms including psychosis and body pain. You can also add 1 tsp of a cooked sesame seed/green tea/milk best method recipe to the plain cooked rice, cheese, greens, milk recipe to calm this effect.>

This drug will continue operating inside the body. Example: The 1 best method in Exhibit D and My favorite best methods in Exhibit G. You must use it as directed. Oil is used for the reason of making this medicine continue in a safe and effective manner. Baking Soda will push out the medicines and cause a psychosis. Green plants mixed with caffeine and milk ingredients or their substitutes are used to make this medicine effective.

Green plants in a drug is good for detoxification. You can add cheese to reduce delusions and psychosis issues and other Visual or other mental impairments such as any delusion. Seed and seed derivatives moving through the body helps remove retardation and stroke symptoms.

Explanation: I use a rice seed in my best method to remove my retardation symptoms. It works almost perfectly on me. The sesame seed cooked with green tea and milk does not successfully remove my lip retardation. I added rice and green plants and oil to maximize the removal of my stroke symptoms. (Please know the retardation or Parkinson's disease symptoms or even a block in a CNS or cholesterol issues are reduced substantially while on this Food.) Seeds that are like Rice can be used.

Seeds and seed derivatives for the mixtures help keep this long term in the body. <Explanation: Rice and the ingredients in 1 the best method for this.>

If overdosing or on a drug or a combination of this patent that is too potent, remove or reduce the caffeine and sesame seeds and purge out the excess with cups of cooked rice and green plants. You can also use milk and a little cheese for a better balanced food.

Cooking these ingredients increases potency. <Example: The Best methods ingredients are made more potent by cooking the ingredients at 2-4 cup milk addition intervals. It increases potency. It also will cause you to get high if you are cooking it like this. It is stronger when you cook it to semi-dry status or dry status like the recipe says with each successive cooking of milk.>

Seeds mixed with caffeine and milk products are a very potent drug. These interchanged ingredients push out malignant cells and toxins. There are many ways and processes to utilize this Interchangeable Patent. <Please refer to Exhibit C>. There are many ways to process this Interchangeable Patent. <Please refer to Exhibit C and B>. Potency and strength and quality can be maximized and increased many ways. This is a drug and a food that is interchangeable. The ingredients are interchangeable.

Using the ingredients will detoxify the body. This patent is a narcotic effect food and a narcotic effect medicine. This is a narcotic drug. A prime example is the sesame seed cooked with green tea and milk in Exhibit D. The interchangeable ways to use this patent and the interchangeable ingredients in this patent are able to reduce the symptoms of many illnesses. The interchangeable ways to use this patent and the interchangeable ingredients in this patent are able to reduce the symptoms of many illnesses continually. A method to push out illness, virus, cholesterol, blockages, toxins, cancer cells, and works to push out illness or disease.

The method of healing the body, Benefiting, feeding, reducing, detoxifying, Increasing or decreasing in potency, decreasing illness, Increasing or decreasing in strength, Changing, Anesthetizing, slowing down, Relaxing, Improving, Stabilizing, Relieving, medicating, continuing or not continuing in a continuum, a food continuing or not continuing, decreasing, burning, pushing out, removing, regulating, sedating, helping, fueling, giving Analgesic benefit, giving Narcotic benefit, and Alleviating many of the symptoms in Exhibit A and Exhibit B Doctor list with interchangeable food, interchangeable processed ingredients, interchangeable pharmaceutical drugs, interchangeable non-pharmaceutical drugs, interchangeable combined Pharmaceutical drugs with these interchangeable ingredients, interchangeable plants, interchangeable seeds, interchangeable Derivatives of Seed, interchangeable organism or human fluids and interchangeable parts, earth ingredients, sub-classes of patents, interchangeable processes, interchangeable methods of use, interchangeable uses, that are Interchangeable and each have their own individual uses, combined uses, methods of use, methods of ingestion, claims and benefits.

Exhibit A Diane Brooks Symptoms and Micah's Too

Cancer; Bumps or tumors in neck in child; undiagnosed Lymph node illness in child; Diagnosed lymph node illness in child;

ADHD Symptoms or ADD Symptoms; Autism Symptoms; Asperger's Disorder Symptoms; Dyslexia symptoms; Alzheimer's symptoms; Bi-Polar Symptoms; Multiple Personality Disorder Symptoms; Schizophrenia Symptoms; Depression; Alzheimer's symptoms; Obsessive-compulsive disorder Symptoms; Dementia Symptoms; Pain Symptoms; Mental Illness Symptoms; Mental Retardation Symptoms; Physical Issues and all other symptoms listed, Phobia Symptoms; other Illness included in this patent; Parkinson's Disease Symptoms;

Mood Problems and Mood Issues; Mood Swings; Anxiety; Anger; (I can't seem to get mad unless it is for only a few seconds on this Medicine); trouble assimilating information, Problems with making sense of information; trouble linking words to their meanings; Problems processing information; trouble paying attention or listening or easily distracted or able to concentrate; Attention Problems and Focus problems and Focus issues; Confusion; Stress; Slowed thinking or processing information; Fast Thinking; Processing information; Trouble following multiple commands; Impatience; Hyperactivity or very fast; talks too much; interrupts or intrudes on others; difficulty sitting still and feelings of restlessness; Jumbled thinking, thought issues, Thoughts: tic, tic, tic, tic: erratic, off, fast; Memory problems; (I still have memory problems. My thoughts are held so still that I have a hard time moving into my memory banks. I can change the ingredients and increase memory); Difficulty reading and understanding sentences and reading and comprehending; Distortions in thought content (delusions); Hallucinations: Hearing, seeing, tasting, feeling, imagining, or smelling things that do not exist; (Small brown or black seeds cooked in Green tea or caffeine with milk solve this. Cheese helps); Disorganized speech and behavior; Losing interest in everyday activities, such as bathing, grooming, or getting Dressed; Feeling out of touch with other people, family, or friends Restricted patterns of interest that are abnormal in intensity or focus preoccupation with certain objects or subjects inflexible adherence to specific routines or rituals; Have trouble sitting still; AUTISM Symptoms: I will be processing large amounts of information and intensely thinking and someone will interrupt me and I react is stress and anger, focus disorder, while it takes the person talking to me a long time to figure things out; Changes in mood or personality; Erratic Thoughts; Reading problems; (With the Rice and cheese in the recipe, my thought are held almost completely still. With wine, greens and flour in the recipe, this ailment is better solved); Restless legs and body; Restlessness; Fear; Panic attacks; Phobias; Perceptions impaired; Compulsions and rituals; Psychotic; Rapid Thoughts; Premenstrual syndrome issues; Menopause symptoms; Mania Symptoms; Increased energy; Racing thoughts; High sex drive; Depression; Loss of energy; Uncontrollable crying; Change in appetite causing weight loss or gain; Sleep issues; (the small seeds when mixed in caffeine and milk help this aliment as well as the best methods); Suicidal; Blood pressure issues; Feelings of heightened energy; Spin out (mentally too fast) of control sometimes, (Manic, rapid thoughts); Delusional; Aggressive; Confusion; Compulsive; Obsessive; Talking so rapidly so others can't keep up; Racing thoughts; Jumping quickly from one idea to the next; Highly distractible;

Eating so fast I think "did I just eat?", which is Impaired judgment; Impulsive;

Acting recklessly without thinking about the consequences; Losing weight; (The medicines will help you lose weight if you purge with Flour and greens in your recipe. Caffeine helps too); Gaining weight; (the medicines will help you gain weight if you use Zyprexa. Mix it with less seed and caffeine and more green beans or seaweed ingredients to better solve this issue. People can lose weight better this way. Zyprexa is horrible as a weight gain drug and you should try to get a better balance using these changeable ingredients. The Best methods are for the symptoms in Exhibit A and it can be changed to help remove the weight gain problem. I lost almost 30 lbs increasing the greens and not using rice and exercising. A High sesame seed and caffeine makes me more lethargic and I gained 15 lbs back of the 30 I lost. The lower the amount and strength of interchangeable rice, sesame seed and caffeine, the higher the energy level); Concentration and memory problems; (I still have memory problems); Overly acute senses smells bother me, sounds too loud;

Staring, while in deep thought, with infrequent blinking; Sleep disturbances; Involuntary movements of the tongue or mouth (facial dyskinesias); Emotional Issues; Hostility; Suspiciousness; Resentment; Rapidly changing moods;

Becoming lost in thoughts and not wanting to be disturbed with human contact;

Replaying or rehearsing conversations out loud; Finding it difficult to deal with stressful situations; Inability to cope with minor problems; Intense and excessive preoccupation with religion or spiritualist; Drug or alcohol use; (any drug use was before 2001. I now use wine occasionally on the weekends); Smoked for 20 years; (The medicines heal the body by placing minerals and vitamins and food medicines and medicines in me); Frequent loose association of thoughts or speech—when one thought does not logically relate to the next; Poor concentration; Forgetfulness; Paranoid delusions; Visual Delusions; Hallucinations; I do not hear voices (only once in my life); Visual hallucinations: All and many types; Apathy; Having difficulty recalling recent events; Having trouble finding the right words to express thoughts or name objects; Having problems planning and carrying out tasks, such as balancing a checkbook, following a recipe, remembering 6 items, or writing a letter; (With the Rice and cheese in the recipe, my thoughts and focus are held almost completely still. With wine, greens and flour in the recipe, this ailment is better solved); Stress: severe anxiety when paying bills or concentrating and someone interrupts me. (I still have this issue, but it is greatly reduced and only lasts for a minute or so);

Organism; The Body; The human Body; Animal body;

Cancer. Lymph Node Neck Right neck mass Cancer: Lymph node with Metastatic adenosquamous cell carcinoma or mucoepidermoid carcinoma, In addition to the usual sites (mucosal surfaces of the upper aerodigestive tract, salivary glands), Two Drs. said: one might even contemplate a carcinoma arising deep within the tonsular crypts. Dr. said there was a spot on my thyroid. 2 Dr.'s said it was not a primary site.; Skin cancer; Malignancy Issues; treatment of malignant cells; problems or issues; Lymph Node problems and Lymph Node illness or issues; Thyroid ($2^{nd}$ Cancer Dr. found said I had a cancer spot on my thyroid and scheduled surgery to remove it and my other lymph nodes and my tonsils) problem (I refused surgery and treated myself); Cell issues; Cell Problems; (In March-April 2008, I refused my $2^{nd}$ surgery 1 week before the scheduled surgery 4 yrs ago. I also refused the mandatory radiation and chemotherapy and made this patent and treated myself with Evening Primrose oils that were heated and placed in Freezer 4 times and processed Fir Bark and Milk and other ingredients and cured myself); cellular deformities; Cellular issues; neck trauma from $1^{st}$ cancer removal 1½ inch cancer tumor surgery; pain; neck pain; Cell illness; Cell healing and all parts of body healing (Evening Primrose oils heated and placed in freezer then mixed with fir bark water and cooked in milk burned out the cancer and treated continually; Cells rebuke toxins; Cancerous (the Dr. said my cancer was found in a secondary place on my neck and there was he had no idea where the primary place was) and non-cancerous cell removal; Lymph Node problems;

Blood problems; Headaches; Symptoms of viral illness; Symptoms and issues that are flu like in characteristic; Gingivitis; Gum and Periodontal disease; bacterial issue excessive endiometric cells;

Fibromyalgia symptoms; Pain; Many tender places on the body that are painful; neck and back and head pain; leg pain; Head Pain; body pain; Muscular pain; Inflammation; fatigue and extreme tiredness; (I have had chronic back and neck pain for 25 years. It is gone. I used to buy the giant bottles of Ibuprofen. I simply rarely take Ibuprofen now.

Retardation; (Rice is an example of what should be added to this patent that eliminates or greatly reduces retardation symptoms). My lip retards and body retards;

Multiple Sclerosis (MS) symptoms; Tingling face; Tingling head; mild to severe Problems with walking; Pain; Cognitive (e.g., thinking, memory) problems; depression; dizzy; Slurred speech; Muscular illness symptoms; Muscular pain; Muscles: blood and issues relating to muscles; Patent helps with issues pertaining to an immune problem;

Palsy Symptoms;

Parkinson's Disease symptoms; Tremor; I have rigidity in the facial muscles; reducing a person's range of facial expressions and resulting in a "mask-like" appearance; Pain and cramping; Posture issues; Fatigue; Impaired fine motor dexterity; Speech problems; Dementia or confusion (I still have memory issues); sleep Issues; depression; fear; anxiety; Memory difficulties and thinking issues; Compulsive behavior; nervous Issues; tremor jerking arm movements; involuntary movements of the limbs; walking not normal;

Bone Issues and problems; Bone Symptoms; 2 Bones fused in neck (does help bone.) It helps build bone; I Cannot say ABC's when I turn my head from left to right (This patent does not help me with saying ABC's from left to right); Bones and back out of perfect alignment (no pain anymore because of this patent); Bone issues; Bone symptoms; Back and head pain; Chronic Back and neck and body Pain; Loss of Bone; Loss of correct bone structure or size or full normal bone construction (Bone is improved by ingredients such as milk) Example: gum disease made my teeth deformed and this patent ingredients helps and eradicates bleeding of the gums and helps bone problems; Deformed spine; Deformed bones; Neck crooked; Neck and right shoulder pulled downward or to right from backpack or purse; Scoliosis; Osteriorporosis symptoms; Neck and back and head pain and interference with all bodily issues; Pain in: many areas of entire body, neck, back, legs, head, jaw; Spinal problems; Diseases; Dental and teeth problems; Osteoporosis; (Temporomandibular Disorder), Blood; Nervous System;

Tardive Dyskinesia; Toxin and toxic issues; blood flow; nerve functioning (when I sit down feel like passing out if my feet are on desk and cholesterol); nerve flow (2 bones fused in my neck and facial, lip, eye, right side of face, butt, back, cheek, arm, leg, hands and body stroke like problem. My medicine alleviates this stroke like problem and symptom.) Passing Out feeling; Imbalance; (Blood Flow and nerves: when I lean forward in my chair or sometimes sitting on my foot, I feel like passing out, blood flow; Back of upper shoulder tingling, going numb, left finger going numb and feeling like passing out; Right Lip drop; Facial stroke like symptoms;

Cerebrovascular Disease symptoms: stroke symptoms; Right eye drops; cheek drops;

Headaches: Gingivitis; Gum Disease; Slurred words; Stress; (facial retardation and lip and head and arms drops like a stroke or blood flow victim and body issues);

Jerking and tingling: arm and hand, body or parts of body;

(Nerves issues: When I stand I cannot touch my nose with one finger, then I straighten my back and cannot touch my nose with the other finger; Blocked nerve issue to the brain is a probable cause of my visual impairments and other problems and issues; nerve flow; Peripheral system and Central Nervous system disorders issues, Peripheral and Central Nervous system disorders pain issues and all other issues; When I am sitting I feel like passing out or when I sit on my foot, I feel like passing out);

Itching; Hives; My vision is impaired as it is dark or black and depth perception is off or weird looking same objects; Leg twitching; Leg aches; leg spasms; Lip spasms; Lip Retardation; When scared I turn red or hyperventilate; Central Nervous system issue; pain issues; Neurological symptoms and illness and acute issues of many neurological disorders; neurological problems; Nerve twitching; Numbness: arm and hand, body or parts of body, brain; Optical issues or Optical part of brain or optical nerve problem; Slurred words; Stress; Pressure in: brain and head and sinus and back of neck and head, temples, cheeks, face, ears, neck and body; Retarded; Extreme retardations; Seizure issue (body, jerking, face, arms, legs, neck, whole and part spinal area, and body and eyes, skin, head, facial drops); Seizure type behavior; Tardive Dyskinesia; Teeth Grinding; Jaw sore;

Vision Problem: Optical issues; Visual: Color perceptions impaired; Visual impairments: Black or Gray scale visual impairments (when I am on my medicines this is eliminated); Visual movements issue (When I am on my medicines, this is eliminated); Drinking or eating or not eating or drinking sometimes causes wave like visual impairments (When I am on my medicines, this is eliminated); Visual Impairments: Many Forms; When I sit down visual impairments or I have black gray visual problems; Visual perceptions impaired; Understanding impaired; Reading impaired; brain or other perceptions impaired; After I correct spine or bone alignment I can see wave like visual issues and can feel blood or something in my head;

Pain: Body pain; Body spasms; neck and back and head pain and interference with all bodily issues, Head Pain; neck pain; leg pain; other pain; Muscular pain; Pain is listed in many areas: please look at it; I cannot wear sports bras (pulls on neck and shoulder area) or sweatshirts with hoods on them because they are too heavy and hurt my neck, shoulders muscle pain from the strain; Pain when I pull on my headboard with one hand, pain for days in shoulder, neck and spine area;

(My best method and the ingredients eliminate or greatly reduce pain when on this medicine. The seed can be made more potent for severe issues. I have had chronic back and neck pain for 27 years and this pain just disappeared with my medicines. I still get the occasional leg pains.)

Cell: Brain Issues; Brain illness; Cell; Removes cancer cells; body healing; Cells rebuke toxins; Lymph Node problems and Lymph Node illness or issues; Malignancy Issues; Infections; Toxin and toxic issues; Removes illness cells; Removes hard masses;

Feminine Issues: Hormonal (I have great and almost perfect moods during menopause); PMS; Premenstrual syndrome; Fibrocystic breasts;

Child with attention disorder issues and problems and This child also has sugar problems or issues (These issues are temporarily corrected by my ingredients); 2 Doctors forced me to take medicine which was Lithium in last trimester (I refused and my MD., OBGYN. called my Psychiatrist and made me. I knew it was bad in first trimester); This child went to a speech therapist and has learning issues (struggles with memorizing abc's and numbers and many other issues like biting her tongues in anger, anger issues, and other issues (The ingredients help temporarily with these issues); She can't slow down long enough and has focus and many other issues pertaining to possible mental illness or physical problems or issues (These ingredients temporarily help with these issues); attention disorder issues; Menopausal problems are almost non-existent (I have minor hot flashes and that is the only symptom of menopause that I still have) since these patents almost eliminate these symptoms and problems and almost eliminate all PMS or menstrual problems and symptoms. I am 50 and probably have gone through menopause; Husband's sexual appetite 1 time per week and mine used to be every 2-3 days minimum, now just 1 time per week. I am married to a normal 53 yr old, one (seldom more) time per week husband; I was always a super high sex drive (when I add 1.5 tablespoons of caffeine into Best Methods, my sex drive is better, Sexual and sexuality problems or benefits or issues (with a high seed drug it causes numbness sexually);

Food: Food deficiency; Chronic weight issues; Eating disorder; Extreme Mineral and Vitamin Deficiency; Food and nutritional problems or eating disorder; problems with eating or consuming food or nutrients or minerals; Food deficiency; Hair dry; Hair illness; Skin and Eyes and body (When I add Oil in my recipes my skin is not as dry and my eyes do not have severe redness or dry issues) Oil is best to be added; Malnutrition; Poor food combinations; Metabolism issues; Mineral problems or issues with; Mineral deficiency; Bone issues; Calcium deficiency diagnosis; Sinus problems; toxins; Imbalance of food;

Bad breath; Detoxification or detoxifying issues; Intoxication issues; Drug induced illness or issues; I was made to take medicines that caused Tardive Dyskinesia in my mouth; Eyes red; Eyes Tired; Eyes dry; Poor vision; Sinus Issues; Slight Hearing problem (the medicine does not help with this except for ingredient nutrition); Pesticide exposures; Snoring; Urinary: Laughing or jumping causes leaks;

These listed issues and all listed above are not necessarily in the correct order, or under the correct heading and can be other issues or illnesses or placed in other areas. No one individual listed or not listed diagnosis can be used to include these symptoms. They are individual symptoms, issues, illness, causes, multiple diagnosis's or problems. These listed are mine and Micah's and Jeff's.

Exhibit B

| Diane and Micah Brooks Diagnosis's and Medical Doctors | | |
|---|---|---|
| Diane Elizabeth Brooks | | |
| Born May 4, 1962, weight 144, height 5' 6", female | | |
| E. M. de Castro, M.D, Surgeon, OBGYN | 503-579-8061 | He made me get on Lithium 3rd trimester |
| Western Psychological | | Psychologist, Bi-Polar Symptoms |
| Linda Sherman, Ph.D | 503-241-5065 | Psychologist, Depression, knew of Lip Retardation. She helped me in Lawsuit. I Told her of Right lip retardation, lip drop in our last meeting. |
| Thomas Lissman, M.D. | He went to work in Corvalis Oregon hospital. | Psychiatrist diagnosed me with Bi-Polar Knew of Lip retardation and Tardive Dyskinesia |
| Bradford C., Ashley MD, MS, MPH | He moved. | Psychiatrist treated me for Bi-Polar |
| Dr. Won Kim (MD, OBGYN, Surgeon) | Retired | Diagnosed me with Anxiety and depression. General Physician and delivered my 1st child |
| Dr. Richard Howell, D.O. | 503-223-6360 | Psychiatrist treated me for Bi-Polar |
| Brett C Corbett, MD | 503-216-9200 | General MD |
| Peter DePaoli, Psychologist Staff: Rhonda Earle, Previous staff Debra Lacey Pastor Clifford Baker | Aloha, Oregon | Diagnosed me with Multiple Personality Dis. I sued all of them because of a false diagnosis |
| Dr. Lindgren | 503-297-1542 | He diagnosed me with Lymph node cancer and surgically removed 1½ inch malignant tumor in my right neck lymph node. |
| Peter E. Andersen, M.D. F.A.C.S, Surgeon, Head and Neck Surgery, Otolaryngology Associate Professor, Director Specialist | 503-494-5355 | Surgeon who diagnosed me with Lymph node cancer. Specialist. This Surgeon was the Dr. who was going to do my 2nd surgery. I refused Chemotherapy, Radiation and a surgery to remove all my upper lymph nodes, thyroid, tonsils and treated myself. |
| Scott A. B. Collins | 503-245-2415 | 1 skin cancer |
| Dr. Harold J. Brelsford, M.D. Surgeon | | Neck and Back pain, found 2 bones in neck fused. 29 years of back and neck pain, scoliosis, severe right shoulder drop. He said the bones were fused at birth. |
| Dr. George E. Hyland Chiropractor | 503-668-5822 | Back pain |
| Chiropractor Beaverton Oregon | | Severe back pain |
| hair analysis migraine hospital tests feet retarded and in corrective shoes as a child | hair sample teenage | headaches and major mineral deficiency Including cat scan and biofeedback. Head Scanned. |
| Dr. Tucker | Retired TMJ Dr. | TMJ |
| Hadi Nouredine DMD | 503-644-1110 | Periodontal disease and dentist |
| Derek W. Conklin DMD, PC | 503-668-4655 | Periodontal disease and dentist |
| Dr. Rizk (Childhood Dr.) | | sinus and severe chronic headaches since I was about 2 years old |
| Dr. Grise MD | 503-622-3325 | Dr. who knew I was having jerking in arms and I thought blood flow issues. I had severe |

| Diane and Micah Brooks Diagnosis's and Medical Doctors | | |
|---|---|---|
| | | retardations in face arms, body and went to see him. He Scheduled me for a Physical. |
| Micah Rose Brooks | | |
| Born May 4th, 2006, 41 lbs Attention Deficit symptoms | | |
| Dr. Grise Mb | 503-622-3325 | Diagnosed Micah July 2010 bumps on neck saw him 5+ Visits for 1½ years. He treated her continually with anti-biotics that did not work on the bumps removal. Bumps still there. The Bumps would slightly change. Size varied and problem is still bumps on the neck that will not disappear. It started with 1 bump and then bumps all over her neck. |
| Sanjay Krishnaswami, MD Pediatric Surgeon | 503-460-0065 | This specialist said that if Micah had her Bumps for 1½ years, she was fine. The first doctor who came in said she would have to have surgery and have it biopsied. Dec. 24th, 2011, The second trip to see this this doctor, both the nurse and the doctor said Micah's bumps were not cancer if she isn't sick. "Feb. 1st, 2011 a large tumor or lymph node, hard like jawbone and very painful popped up. It was a large 1½ inch very hard bump on her jaw. I treated her 5 days with non-drug food ingredients in Exhibit G, The Uncooked Version. It reduced to almost ½ the size within 5 days. Within 9 days this bump disappeared. Within 8-9 days almost all the bumps on her right side of neck completely disappeared. After 12 days, there is only 1 lymph node still enlarged on the left side and a small one on the right side. All the many other bumps that have been there for 1½ years GONE. One Lymph node was difficult and I added more greens and it was reduced in size. |

Exhibit C

Ways to Use

Uses that have been Tested

This is Just a Sample List and not Inclusive

1. Ingestion (Inhale it). 2. Add it to existing patents or non-existing patents and other combinations of ingredients that can be produced with these ingredients 3. Eat it with medications 4. Eat it as food. 5. Intravenous 6. Add it to Food and use as a normal additive. 7. Use it as Bread. 8. Use it in a casserole or bar of food, 9. Ingest it as a drug. 10. Ingest it with other drugs 11. Use other medicines with it. 12. Heat it inside the body 13. Cook it inside the body 14. Process it inside the body 15. Cook it with dirt or sand or volcanic rock and eat it. 16. Consume it in sand 17. Consume it in a cup of oatmeal or dirt 18. Chew it. 19. Shake it or agitate or grind it and drink it 20. With protein, meats, fish, poultry, and other substitutes and oranges 21. As a continual daily dose 22. As a Continuing food that needs little to continue 23. As a continual Medicine or non-continuing medicine 24. As a One time dose 25. As a many times dose used daily (or semi-frequent) 26. Continually 27. As needed 28. Dry or Powdered 29. Wet or Uncooked 30. Cooked or Not cooked or heated 31. Mixed or unmixed 32. Mixed in the body 33. Processed in the body. 34. As individual ingredient portions on a plate, then consumed 35. As a cooked medicine 36. As an Uncooked and Undocumented medicine 37. As a seed eaten after it has been soaked in ingredients 38. As a seed and it's derivatives and as a green plant and as bodily fluids or parts 39. As a mixture of ingredients or substituted ingredients 40. As a part of a continuum 41. To combine with other Pharmaceutical drugs, plants, medicines or combinations thereof to make new medicines, drugs, patents, subclasses of patents 42. As a strong medicinal food or medicine 43. As a food 44. As a drink 45. As a vitamin drink 46. As a mineral drink 47. As a health food drink 48. As a health food 49. You can just sip it in green tea or caffeine 50. You can sip it in coffee or chocolate milk or other black teas or green plant mix drinks 51. As a potent drug and very strong medicine 52. As a seed planted in the ground then eat the dirt and entire plant 53. As a Sesame seed or evening primrose seed or other seed or seed derivative or plant planted in the ground then pour milk into the dirt and add caffeine to fertilize the plant and eat the dirt and entire plant 54. Consume daily. 55. Distilled 56. Processed 57. In a continuum 58. Wine or Beer processing plants will make these ingredients and I can sell it like this 59. Cereal companies can make this and I can sell it to the people 60. I can place it in a morning chocolate oatmeal bar or many other ways 61. Cooked with alcohol 62. Uncooked with alcohol 63. Cooked or uncooked with fruit 64. Served with alcohol and enjoyed 65. Cooked with vinegar and fermented ingredients 66. Served with Vinegar and fermented ingredients 67. Uncooked with vinegar and alcohol 68. Use a drug Companies additives (Propylene Glycol I used.) 69. Use additives 70. Use foods that add to this 71. Use plants that add to this 72. Use seeds that add to this 73. Use bodily fluids that add to this 74. Use meats, fish or poultry that add to this 75. Add vitamins and minerals 76. Add sand minerals 77. Add the earth minerals 78. Add food or plants 79. Add mixes or combinations of ingredients or combinations of additives 80. Add other substituted combinations that are not food but help with the food or patent ingredients or parts thereof mixing to achieve the healing claims in this specific patent. 81. Substitute patents that can be added and watch this turn into new foods, medicines or new patents. 82. Add new substituted ingredients 83. As part of a tree (fir Bark was used) 84. As a flower 85. As a flower and all parts of this shrub. I used every part of the Evening primrose plant and processed all parts and consumed all processed parts. 86. Make it a liquid 87. Make it a gas 88. Make it a solid 89. Serve it as wine 90. Serve it as alcohol 91. Nutritional supplement. 92. Cancer treatment 93. People can make it in their own kitchen 94. People can make it in their own backyard. 95. People can pick their own Food up out of the worlds' abundant source of plants and use their own body or animals milk 96. Cook it in a firepit 97. Use 2 ingredients and process them 98. Use 2 or more ingredients and process them 99. Cooked 100. Heated inside the human body 101. Inside a continuum 102. Inside a machine or system 103. Inside a body 104. Sickness remover 105. Claims for resolving exhibit A and illness 106. Illness remover 107. Make it Beer 108. Make it wine 109. As a hot whipped drink 110. As a coffee or a caffeine or a energy drink 111. As a drink 112. As a food 113. Eat foods processed with the ingredients in this patent in it; 114. Eat foods with the ingredients in this patent in it; 115. Eat foods combined with the ingredients in this patent in it. Example: Go to the hot coffee section of the grocery store and get a cup of hot, hot water and put 2 green tea bags in it, put in 2 large pinches of fresh green cilantro in it and pour in 1-3 tablespoons of sesame seeds. Put the lid on it. Let it set for a little while. Consume until you feel better, throw the rest away); 116. Drink milk or little coffee creamers of Half & Half 117. Drink chocolate milk 118. Combine seeds, green tea and greens and cook it 119. Eat fruits such as a handful of figs 120. Eat the combined ingredients Exhibit D Best Methods Continual Medicines can be removed by Detoxification. If you are overdosing or feel like you are so high you can't come down, eat 1-2 cups of cooked rice covered in milk with ½ cup of green beans or other green and add ½ tsp of sharp cheese, 2 tsps of olive oil or oil and a half or more cup of coffee. Later do the same. Later, do the same. You will notice that in a day you will be better. Continue one time daily or more if needed. Keep the daily best method diet below or this one. It is also best to always add a best method sesame seed/tea/milk combo to slowly detoxify with this food combined, but for rapid detoxification, please just use the above food and eat lots of it continually (with no or little caffeine. Stop drinking your regular caffeine drinks). You will be very high for a day, but it will gradually decrease and you will detoxify this narcotic based medicine.

Every Best method should have a little oil. I use 1 tsp to 2 tablespoons of oil per dose.

The Best methods do not have to be cooked at 2-4 cup intervals. It increases potency. It also will cause you to get high if you are cooking it like this. It is stronger when you cook it to semi-dry status or dry status like the recipe says with each successive cooking of milk The Best method is best if consumed daily. Once you get accustomed to the Medicine by taking 1 cup per day for many days with hot milk for breakfast for 3-4 days then lower the dose to $\frac{1}{3}^{rd}$ to ½ cup, per day then keep that dose steady for a few days then lower it again to 2-5 tablespoons for a few days, then gradually to 2 tsps to 1 Tablespoon per day of the actual Best method recipe (with or without Zyprexa cooked in it). I just reprogrammed your cells. (I usually do not eat anything but this medicine in the morning. This medicine has a chance to move through my body. I do drink 2-3 cups of coffee. It is not necessary, but helps.)

The Best method for most of my illnesses is using a rice seed with a sesame seed, for the right mix, out of all the other flours available. I add sesame seeds, rice, and the interchangeable seeds with green plants, milk, caffeine and cheese cooked together for my mental, physical and pain issues serious lip and body retardation, and mental and physical illness symptoms. The seed allows this medicine to last longer than just a green plant best recipe. I always add a tiny amount of cheese to help eliminate delusions. I always add a little green plant parts to make this medicine and push out the medicine. I add a little tiny bit of oil to keep this recipe from causing imbalances and I prefer no oil. Adding a whole lot of oil separately will cause this recipe to continue a long time in the body. These are best method uses.

I always drink hot coffee in the morning to stir up my medicine and make this medicine balanced. I stop drinking coffee if the medicine is too strong. This is for the coffee addict: I use a medium strength coffee. Do not use strong coffee. If you have strong coffee, mix it with ½ water or use ½ the amount to make the pot of coffee. This is a general guideline and not mandatory with the Best methods listed here. You make an imbalanced drug if you consume strong coffee all day with these best methods. Make sure that if you notice a possible "not strong enough drug in you" to increase your caffeine intake. In other words, have another cup of coffee.

Do this in the evening if needed. The coffee should be a regular drink I noticed that when I cut my coffee to ½ water and ½ stronger coffee water, my drug was not strong enough in the evenings after I had eaten regular food all day. Work out your own coffee balance.

The Best method recipes below includes quantities that I have found to be the best methods. I spent 5 years balancing these ingredients and perfecting these quantities and ingredients. (The delicate balance of ingredients and their quantities makes this recipe unique. You need to rebalance your medicine if you drink wine. One glass of red wine detoxifies me mildly the next day. I love adding one glass of wine. I then need a little more medicine or best method to stabilize my mind. Too much rice or greens or sesame seeds or caffeine can cause huge irregularities in the medicine.)

Pharmaceutical companies will make these much more potent because there are many methods to increase potencies and change these into very strong drugs.

I have made these into very potent drugs, but I hate the really strong versions. You need a balanced food that does all of it and I have found this combination to be my favorite. Skip the stoner drugs and keep it mild but just strong enough to do the job. You can make seed and what is derived from seed very potent or very weak My best method, which is a daily food, is for the sick person to use daily with very low potencies. It is a breakfast for the sick Add Meat, poultry or seafood to this and you have a new best method. The Best method for my reading and focus issues are greens cooked in green tea and milk and consumed. This method does not last as long as my seed recipes.

I love the Seaweed cooked with green tea and lots of milk Cook until dry and you will love this.

The Best method for making a drug basis and strong medicines and much more potent medicines and for most of my illnesses listed in the Exhibit A is to add Sesame seeds, Fir Bark (cooked in water until dark Fir water is used) or poppy seeds then add strong green tea and cook it in milk until dry and adding more milk and cooking it until dry numerous times as in the claim list. This is the way to make your medicines. (It is part of the 1 Best Method) Digesting this daily will build it up inside so you should reduce the quantities to 1 tablespoon per day.

The Best method for removing cancer is to eat these recipes daily and add a 4 time cooked and placed in freezer Evening Primrose oil with this medicine and eat it every day. You need much of this processed oil to be in your body. Reduce oil quantities after your cells are full.

The medicine can be made more potent by adding more sesame seeds into your recipes and cooking it with the listed ingredients.

The medicine can be made more potent by adding stronger tea into your recipes and cooking it with the listed ingredients.

This best method medicine can be consumed daily or used as a continual drug or a continual drug with a daily balanced food and it can be purged out of you with a detoxification.

Please note that a mistake I made in this process was using a cheap green tea. Please use good ingredients. You cannot achieve a great drug unless you use the best ingredients. Example: Don't use skim milk Don't use dollar store or low caliber green tea. Don't use ingredients of a lesser caliber. You can make these drugs out of low grade ingredients, but if you do not have a strong green tea or a good milk or seed, it may cause psychosis or just not work properly. Example: don't use Minute Rice. I love McCormicks sesame seeds.

This is a Basis Best Method

It can be Used by Itself or Placed in the Best Method 12 sheets Dried sushi seaweed or 1 cup green beans Take 2 Tea bags of Stash Premium Green tea to 2 Tablespoons of Green tea cooked in water until dark. Use only dark green tea water and discard the actual green tea. You may also interchange the green tea with freshly brewed coffee by pouring in 2-5 cups of coffee. Add the greens and green tea water or coffee to 4 cups of milk and blend it.

Cook until almost dried.

Repeat 7-10-times adding 1-4 cups of milk and cooking it until dry.

Take 1 Tablespoon per day or more or less with hot milk and coffee. Please note that green plants can be used instead of Seaweed or green beans. I have used many green plants.

This is a Basis Best Method

This is My Best and the One You Need

It can be Used by Itself or Placed in the 1 Best Method 4-6 Tablespoons of Black Sesame Seeds or Blonde Sesame Seeds or Poppy Seeds Take 2 tea bags (I use 3 Stash Green Tea bags) of Stash Premium Green tea or 2 Tablespoons of Green tea cooked in water until dark. Use only dark green tea water and discard the actual green tea. You may also interchange the green tea with freshly brewed coffee Pour in 2-5 cups of coffee. I only use 1 Tablespoon of green tea in my favorite mix.

Cook the greens and caffeine drink into 4 cups of milk and cook until almost dried.

Repeat 7-10 times adding 1-4 cups of whole milk and cooking it until dry.

Take cups at first for days, then slowly reduce to 1 Tablespoon per day or more or less with hot milk and coffee. This may takes weeks to fully acclimate the body. Please note that other seeds, grains, plants and fir bark water can used instead of Sesame seeds and poppy seeds. I have used Fennel seeds and Evening primrose seeds and others.

This is the Best Method I Used Every Day

The Best Daily Method for Exhibit A

1 Best Method

Interchangeable with Jan. 29, 2009 Communion Recipe Prophesy

8 Tablets (20 mg each) crushed Zyprexa) Add more if needed.
 (Interchangeable with: 80 10 mg or higher Lilly Zyprexa Zydis crushed
Tablets.
This recipe works without adding a Pharmaceutical drug. Interchangeable:
Here are 2 different drugs. It works with and without an added drug or medicine.
3 Tablespoons Blonde Sesame Seeds
 (Interchangeable with: 3 Tablespoons of Poppy seeds, Evening Primrose Seeds, Poppy Seeds or Black Sesame Seeds.) 2 Tablespoons of sesame seeds was great for me not ground up but just placed in the recipe as is. Grinding them allows me to lower the dose of the sesame seed to 3 tsp or 1 tablespoon. I found 4 tablespoons to be too strong for me.
4 cups Black brewed coffee Straight from the coffee pot. Just pour it into your recipe: 4 cups of caffeinated coffee. (Interchangeable with: Brew 2 cups of water and 2 Stash green tea bags to 1-2 Tablespoons green tea. Boil for 15 minutes and add 2 cups of water and brew for 15 minutes, let set 30 minutes (or much longer) and remove the actual tea (bags) and only use the dark green tea water. I prefer using ¾ths Tablespoon to 2 tsp of green tea to 2 Stash green tea bags to make my dark Green tea water as my quantity and caffeine preference.
1 tsp Olive Oil (Interchangeable with Evening Primrose oil) and add meat
2 tsp frozen green beans (Interchangeable with Broccoli or Dried Sushi seaweed) Grind the greens, but not needed. (I can add up to ¼$^{th}$ cup of greens)
½ cup rice (Interchangeable with Whole Wheat Flour, sweet rice, Long grain Brown rice.) Powderize the rice for best results. I prefer plain rice in my recipe.
3 Tablespoons Sharp Cheddar cheese (I use goat cheese or strong Cheeses. Medium cheese can be used. Interchangeable with: Red wine. Just pour in one bottle of good red wine) I prefer cheese and not wine.
Add 4 cups of milk, stir and cook until almost dry. (Interchangeable with other Milk ingredients such as evaporated milk, cream, and sperm).
Add 8 cups of milk, stir and cook until almost dry.
Add 4 cups of milk, stir and cook until almost dry.
Add 4 cups of milk, stir and cook until almost dry.
Add 4 cups of milk, stir and cook until almost dry.
Let set to dry or freeze. If dried, it will store outside a freezer. I usually keep it almost dried and freeze it and just take my daily portion from the freezer. (I usually quit here, but you can add 1 cup or 10 cups of milk for better medicines. Add more milk and keep cooking it for potency and doses to be changed)

I always consume my daily dose with 12 ounces of hot milk. It is important that you consume ½ tsp of oil per day, minimum. I use more if I have an imbalance. Do it with your daily dose. You need it. It keeps the food from getting out of control in the body.

Take 1-2 cups of this per day in the morning with hot milk. Then lower your dose. You can just eat ½ to ¼$^{th}$ cup to cups per day, then reduce the daily dose a tablespoon or more or less daily (with hot, milk in the morning) or quit taking this period. Do this repeatedly until your whole body is filled. Then lower the dose to 1 tablespoon or less or more per day (depending on how many times you add milk and process it.) Take this daily in the morning with hot milk. This is my favorite way to consume this food. (It takes about 3-10 days to balance. As with many medicines, the first 5-10 days (approximately) of balancing this in your body may cause some psychosis. You will notice that it almost completely disappears shortly after this initial body acclimation period. Your brain has to regulate this. No big deal. After I have regulated this food recipe in my body, I consume normal food and never too much of one ingredient. Just keep your diet in balance. I find I cannot eat cheese as a snack unless it is balanced with other foods or it will cause a temporary psychosis. I drink 3 sips of evaporated milk if I drink too much coffee.

You just need to eat normal foods and not too much of one ingredient.

You need to keep taking this medicine until your body is filled so if you quit consuming the medicine, the medicine will continue. Redo as needed.

Interchangeable Ways to Use this Patent:
(This is Lust an Example of Some Ways to Use this Patent and it is Only an Example of Methods of Use):
1. A daily drug by taking a Tablespoon or Two tablespoons plus or minus daily (After the initial higher doses to acclimate the drug in the body (or just add a little to the uncooked version in Exhibit G)
2. Add a Pharmaceutical drug or recipe to it to change into the drug you need. Make a continual drug by taking it and making it regulate in your body and then Stop taking it at all and balancing it with food. It is not needed but it is a best method to eat an Interchangeable balanced food of the Best method.
3. Removing this drug by a detoxification method.
4. Remove the drug effect and only use as food.
5. Remove the oil and eat naturally.
6. Remove the food and only make drugs.
7. Allow it to naturally remove itself.

Continual medicine is when the food acts continually inside the body and medicates. This 1 Best method and favorite best method of mine does that. The drug will be able to be removed. You Simply eat the same ingredients in large quantities as a food medicine. It is also best to not use green tea or caffeine. You should avoid potent seeds and potent grains and you should always understand that a person might become psychotic on a detoxification.

An example of a food detoxification is a cup of cooked rice, 3 long skinny green or more beans or more, a tsp of cheese, 3 cups of milk, no sesame seeds, no coffee or green tea, no oil. This is a basic one. You can experience psychosis with this recipe when used daily.

The other option is to just eat normally and eat these ingredients.

Another option is to cook 1 tsp of processed sesame seeds (cooked in water and 1 cup of coffee with 7 cups of milk. Cook until dry and store in the freezer). Add 1 tsp or Tablespoons into these detoxification foods only if you have problems with a detoxification.

Interchangeable Balance Food of the Best Method and a Wonderful Balance Food for Exhibit G (Use when You Stop Taking the Medicine to Make Your Medicine Balanced or as a Food to Keep Your Medicines Balanced.)

Do this if you feel your medicine needs a little more balance. Please eat this as a daily interchangeable Food.

Daily eat 3-5 tablespoons of cooked rice seed, 1 chicken egg (Interchangeable with quail eggs or meat), 1 small pinch (1 tsp to 1 full tablespoon) ground sesame seeds if you need it for potency, less is better. Interchangeable with dark Fir bark water or Poppy seeds), ¼$^{th}$ to 1 tsp of sharp cheese, ½ tsp or 2 little pieces to 1 tsp of green beans (Interchangeable with Seaweed or ½ Tsp of green Broccoli), 1. cup of Vitamin D milk, my normal 5 cups of coffee per day (Interchangeable with Green Tea), 1 tsp of olive oil (Interchangeable with Evening Primrose oil). Use more if needed. Always have oil for a continuing drug that works best and more if needed. I eat this uncooked. The only cooked ingredient is the rice. I combine the ingredients and heat it up in the microwave. Sesame seeds or poppy seeds can cause extreme potencies. Do not use too much. It could feel like you are overdosing. Always decrease sesame seeds or poppy seeds and caffeine to lower potency levels.) I always have 2+ cups of coffee in the morning and I drink 3 cups per day and if needed one cup of coffee before bedtime. If I am having psychosis in the am, this immediately solves the problem and regulates me. I drink milk and juices to help this medicine. I always eat meat to make this medicine very strong if on a continual medicine and not taking it daily. Meat helps either way though. I snack on foods that have a little rice or seed, cheese, green plant, milk, oil or other ingredients like egg and juices and meat. This can be a great method of balancing yourself.

You may end up doing it 2-3 times per day if you have an imbalance. Extreme Psychosis can result if an imbalance is not regulated.

(I hate doing this 1-3 times per day, so I prefer the 1 Best Method recipe or the Favorite Best methods of mine that is a drug version and taking a tablespoon every morning with hot milk).

If you are still having an imbalance cook this:
4-6 Tablespoons of Black Sesame Seeds or Blonde Sesame Seeds or Poppy Seeds (I prefer Sesame seeds.)

Take-2-4 Tablespoons of Green tea cooked in water until dark. Use only dark green tea water and discard the actual green tea. (I only use 1 tablespoon of Green tea when cooking this.) You may also interchange the green tea with freshly brewed coffee Pour in 2-5 cups of coffee.

Cook the greens and caffeine drink into 4 cups of milk and cook until almost dried.

Repeat 7-10 times adding 1-4 cups of milk and cooking it until dry.

Daily Dose:
Take 1 cup to 5 Tablespoon per day at first for a few days. Then use a little less. I use 5 Tablespoons with hot milk and it makes me sane within a few days. It can be lowered. Consume with hot milk and coffee. Please note that other seeds and grains can be used instead of Sesame seeds and poppy seeds. You may also cook down Fir Bark in water and only use the bark water in the recipe. I have used Fennel seeds and Evening primrose seeds. Freeze the batch.

Another sample daily dose is: Take 1 (or up to 5 Tablespoons if you need it) heaping. Tablespoon of this above cooked and processed sesame seed/caffeine/milk-batch and then add 12 ounce of Milk, $\frac{1}{4}^{th}$ tsp plus $\frac{1}{2}$ of $\frac{1}{4}^{th}$ tsp of strong aged cheese, 8 large green peas, 4-6 tablespoons of cooked rice, and heat it in the microwave and consume this. This will be a good food. Do this as your breakfast. Drink coffee.

This is not the best way to use this. The best way is to eat the Favorite Best Method that I use every day and place the actual medicine back in your body. Redose at 1 cup per day for 3 days then lower the dose to 1/c cup then $\frac{1}{3}^{rd}$ cup, until you get to 1 Tsp to 1 tablespoon per day of the BEST METHOD I use daily recipe.

You do not need Zyprexa with this recipe. Just don't add any Pharmaceutical Drug and it will still be effective. You can substitute other medicines, plants, drugs, combinations thereof and other patents, ingredients or substitutions into this recipe before or after you cook it. I added simple aspirin to my medicine foods. You can cook it into your recipe. You can add Pharmaceutical Drugs, herbs, drugs, Medicines to this original recipe and thus make new drugs. Combine them in the original uncooked ingredients and cook it all together. You will always know that governments have already approved these drugs or they would not be on the market. Always check the warning labels on these medicines before adding them to this food. Never add one that a certain food in this recipe cannot mix with safely. You can eat this daily as a daily food.

You can choose to stop taking this and make a continual drug. It is best to eat the ingredients in small portions per day for best drug continuance. This is extremely unique. You can just make a basic new drug or a continual drug. Uniqueness is the accurate and new drug you can make with many Pharmaceutical medicines or non-pharmaceutical drugs and other additives combined with my patent.

Always make sure your body is full of this medicine before you lower the dosage.

This is a balance food. Let us keep the balance. Too much of any green causes psychosis as it pushes out the medicine. Do not panic. Just re-balance your foods and add more sesame seeds. Eat grains, but just be aware that you may need to adjust your medicine dose. I have a mild visual impairment in the morning from my illness, but as soon as I have coffee, it goes away. By adding Zyprexa to the recipe of The Best Methods, you can decrease this mild psychosis and add any benefit Zyprexa has inside it's medicine to this patent. A stronger dose of sesame seed like 3 tablespoons in the medicine recipe (instead of 1-2 Tablespoons) would work great, but I do not like too strong of a medicine. I use coffee every morning as a 'stir my body up medicine.' Drink evaporated milk to help you acclimate and make this medicine make you feel much better. Caffeine is a wonderful food. Tea, Coffee, Oil, Evaporated milk, Chocolate, meat, wine, eggs, and other ingredients that make this a better medicine. You can eat these to help subdue any issues that arise from an imbalance in the food. I choose to eat it as is and use meat and it's substitutes. Meat can be any crawfish, chicken, protein powder, lamb, beef, or other substitute. You can thwart off imbalances in the medicine this way. It naturally purges the body and makes the medicine move through you and you will feel much better. Meat is a perfect addition. It can be added directly into this medicine. (All the additional or substituted ingredients can be cooked into this recipe, but it is not needed. Eggs help this drug. I could add eggs and meat into a food bar and serve it.)

Add a medicine in your needs such as aspirin, Zyprexa, and other anti-psychotics. You don't need your full medicines in this, just a few pills or many pills.

Best Methods do not need Pharmaceutical drugs cooked into it. You can blend them in. This is one way to make them. There are many ways. You could just eat it with the Best. Method. They are wonderful without.

The Best "Best" Method is to add more Seed and Caffeine. You can adjust the strength of the drug with more Sesame, poppy or Evening primrose seeds cooked in more green tea or coffee and milk. Create a basis that is very important. Take a small amount of Black sesame seed or interchangeable seed and boil it in a strong Caffeinated green tea and 3-6 cups of milk. Add more milk and cook again. Repeat if needed. Heat and dry it. This is a drug.

Other Best Recipe Methods (My personal favorite recipes are in Exhibit G):

1. To my Sick Children everywhere:
   You can make this as a Continual Drug made out of Unleavened bread in your oven. Just place ALL the ingredients in a large pot in the oven. Add all the milk (24 cups) in the Favorite Best Methods or Best Methods (Exhibit D and G) recipe at one time and just cook all of it at 350 degrees stirring constantly until dry instead of only cooking in 4 cups of milk at a time. (Heck we could make this in a bread machine!) You never have to grind the seeds or powderize them. Then eat cups per day with hot milk and lower the food dose as instructed with a dab of oil. (ps. I ate this and lots of it, then quit taking it and 5 days later it is stronger in me than it ever was . . . . A Strong continual medicine. But, I still prefer the milk cooked at 4 cup interval medicine. The only cooked once version does not give me the all day strong anti-stress and narcotic benefit. It is just not quite good enough for me. I wouldn't use the uncooked version either. My illnesses require something strong. I need this drug stronger. I have a stress issue. Heating and cooking the ingredients all the way then repeating that action over and over again enhances this medication.) Then have a couple of cups of coffee and eat my balanced food daily. It works. It is Unleavened bread with a sprinkle of cheese and a little green plant in it. This is Unleavened bread with green tea or java. Either way, this is UNIQUE and this patent is Expressly UNIQUE.
2. Another Best Method is to take all the ingredients in the Best method recipes and to simply place them on a plate individually and consume them. Do not mix them. You can then cook them and eat them.
3. Another best method is to take the ingredients in the best method recipes and place them individually on your plate and drink the milk individually and individually eat them as you would a Thanksgiving dinner. (Or do the blender mixed version like my daughter Micah ate in Exhibit G)

1 to 7 Ingredients that are each interchangeable that are processed and combined many ways to heal and alleviate symptoms of illness and these combinations can be added to Pharmaceutical drugs, medicines, ingredients, mixtures, elements and these combinations can be made to continue or not continue means this continual medicine and it's effects can be reduced by consuming these uncooked or only slightly cooked interchangeable ingredients as a steady daily food, with little caffeine, until the strong effects are naturally eliminated from the body.

Exhibit E

Processes

Sample of Some Interchangeable Processes

Sample List of a Few Processes Used to Make this Patent

This patent can be processed or made many ways. It is interchangeable. It can be heated in a firepit or in a microwave. It can be cooked on a stove or in an oven or processed and heated in the human body. It can be combined by blending it in a blender. It can be chewed by a human. The seeds can be whole, powderized or simply crushed. It is processed inside the human body by heating it inside the body or combining the ingredients inside the body. It can be frozen. It can be powderized or eaten as plain seed. The seed and seed derivatives can be made more potent by adding caffeine and milk, blending it, shaking it or cooking it. It can be made more potent by adding more milk and cooking it. It can be made as a simple food or as a very potent food that has a narcotic effect. It can be made into a liquid or a solid or a gas.

There are many ways to increase potency: Fertilize the ground to make each plant more potent or any method of making potent plants or by processing your recipes by oxidizing them or letting them cure, Making the ingredient into a powder or processing the ingredient differently, or processing them in a heated area or inside the body. Use any process that is on the market to process these recipes. Potency can be increased by adding ingredients such as just using seaweed and milk is effective, but when you add green tea you get a very potent medicine or when you add sesame seeds or other seeds you also increase potency. Potency can be increased by using more of the ingredients such as milk and cooking it more. Potency can also be increased by agitation. Cooking these ingredients increases potency. Potency changes with ingredients and cooking times. Potency changes with the amount of sesame seeds used. Process it as beer or wine.

Exhibit F

Examples of Some Interchangeable Ingredients

Examples Only of Some Interchangeable Seeds

Some examples of some of the seeds used: Seed definitions.

Seeds should be a hard shell and size does not matter, but small brown, black or blonde seeds have proven effective. This is not a requirement. I use bark from trees that all come from seeds. Soft seeds work great. It is a seed also. Bark is not small, but for these recipes, I have used small seeds. I have interchanged many dark, small seeds. My best methods use a combination of small semi-hard seeds and hard rice. White seeds are great also. Soft seeds work great. Some seeds I have used are: Rice, Jasmine rice, White rice, Brown rice, Wild and brown rice, Minute Rice, Wheat, Oatmeal, Black Sesame seeds, White or Tan Sesame seeds, cocoa seeds, coffee seeds, coffee, tea, green tea seeds, Fennel seeds, Poppy Seeds, Evening Primrose seeds, Green, red and white bean seeds, peas, kidney beans, protein, beans, wheat flour seeds, white flour seed, grains, garlic, Fir bark, Wheat germ, potato starch, corn starch, Life Cereal, Frosted Mini-Wheats, starches, vanilla, spores, moss seed, eggs, mayonnaise, sperm, Santiam Classic Marinated Three Bean salad, barley, flax seed, green tea seeds, pistachios, Examples Only of Some Interchangeable Processed Ingredients Apure Foods Co. EatThinkSmile Cinnamon almond granola Clusters (cocoa, whole grain oats, palm oil, rice, almonds, malt barley flavor, soy lecithin, salt, cinnamon, cane juice); Dark Chocolate bars; Zyprexa; Zydis; Aspirin; Mayonnaise; Santiam Classic Marinated Three Bean salad, Wheat germ; wine, alcohol; Evening Primrose oil Cold pressed; propylene glycol; evaporated milk, milk pulp, dried milk, cream; cheese; coffee; Energy drinks; hot chocolate; Fig bars; canned fruit; beer; oil; unleavened bread; leavened bread; Half & Half; Sour Cream; butter; (Eat foods processed with the ingredients in this patent in it);

Examples Only of Some Interchangeable Green Plants and Examples of Other Interchangeable Plants and Examples of Seed and Seed Derivatives Some examples of Green plants used:

Moss, clover, clover stems, Evening Primrose green plant parts and parts, broccoli, green teas, rosemary, cilantro, turnip greens, spinach, pistachios, Seaweed, Green beans, green peas, Seaweed, Green grass, green beans, cilantro, jasmine green tea Some Examples of Seed and Seed Derivatives, Plant and Earth Samples and Interchangeability Some examples of ingredients I have used:

Bark water, tree branch, Fir bark, Flowers, chocolate, fruit, Powdered Primrose powder, Evening Primrose oil, Evening Primrose seeds, Sesame oil, Olive oil, First Street oil, Black tea, olives, Evening primrose plants (Entire plant), salt, sugar, dried grass, carrots, plant roots, stems, full plant and shrub ingredients and parts, parts of the plants, flowers, honey, aspirin, Rose petals, flowers, Salt, Rocks, volcanic ash, sand, dirt, protein, cayenne pepper, vinegar, wine, alcohol, starches, corn starch, potato starch, baking soda, vanilla, oil, ibuprofen, fermented plants, garlic, Zyprexa, Zydis, Lithium, Aspirin, Ibuprofen, Fermented fruit, fermented rice, fermented seeds, fermented recipes, fermented grains, fermented milk, fermented cheese, fermented body fluids, propylene glycol, food additives, mold, fruit, ripe fruit, mold, prunes, cheese, fruit, Tea, coffee, chocolate, Coca Cola, Soda, green plants, non-caffeinated tea, decaffeinated teas, cocoa bean or chocolate, Black tea, caffeine, plants with caffeine, Dr. Pepper Cherry Cola, Examples Only of some Bodily fluid and body parts used: milk, evaporated milk, milk pulp, dried milk, cream, sperm, vaginal fluid, sour cream, honey (Made from bee spit), saliva, spit, cheese, meat, protein, fish, crawfish, eggs, mayonnaise, bodily fluid, human body, human body fluids, cat body, animal body, chicken eggs whites or yolks or both with or without sperm from rooster fertilization, ice cream, sour cream, Examples Only of some Oils I have used: Evening Primrose Oil, Sesame Seed Oil, Saffron Oil, Olive Oil, Mayonnaise, First Street Oil, Wesson Oil Examples only of minerals, clay, dirt, ground, sand, rock, metals, vitamins, volcanic rock, volcanic ash: Sand, clay, dirt, rock, soil, metals, vitamins, ground, a combination of these and any single one, silver can be added.

Exhibit G

My Favorite Best Methods

A favorite DRUG Basis:
Do this and just eat the food ingredients to balance this:
5 Tablespoons Sesame seeds (place in coffee grinder and powderize or grind)
5 (Stash brand) green Tea bags. Boil these tea bags, in the microwave, in 3 cups of water for 15 minutes. Smash down the tea bags and let set for 15 minutes. Drain the tea and discard the actual green tea and ONLY USE the green tea water.

Add ½ cup of Vitamin D whole milk into the mixture and microwave until dry. Add ½ cup of this same milk and cook in microwave until dry. Do this 12 to 20 times). Place it in a baggie labeled medicine do not eat and store in a freezer if you can. Consume 1-2 cups per day with hot milk for 1-6 days. You must have enough in you for this to work, then lower the dose to ½ cup to lower until you maintain at 1 tsp to 1 tablespoon or 2 tablespoons per day.

(Eat a little grain (such as rice) with 1 green bean and 1 tsp of cheese (sharp), a glass of warm milk, and a tsp of oil or less per day. Eat meat and eggs and drink hot coffee all day. Please use a coffee that is not too strong for best results. I am a caffeine addict and I have balanced this medicine through good medium coffee. If you choose to exchange these ingredients, you can. This is a best method. I really don't even eat like this. I just eat the recipe and drink coffee.) This is more of a detoxify recipe with a hint of stability. I prefer 1 Best Method as my favorite.

My Favorite Best Method Uncooked Version

It is Good for Almost all My Symptoms and Micah's Too

A best method is a drug that can be used as a continual medicine and a food.

An uncooked version of food (described below) can be eaten by children and removes hard and many bumps in lymph nodes or on the body. You can make the patent very potent. You do not always need high potency. Please note that you can add meat to these methods. This is best as food. The food still works and you may make it as strong as you need. You will use 1 Best method for a higher potency needs and the food uncooked (but heated for 50 seconds in microwave) version for everyone. This recipe is a good recipe for almost all my illness symptoms. I used the uncooked version on my daughter and eliminated a 1½ inch hard bump attached and loose behind her Jaw to ½ the size in 5 days and completely gone by day 12 and all the bumps on the right side of her neck completely disappeared in 12 days (only one tiny almost unnoticeable one was left on the right side and one same size-non-reduced bump on the right after 12 days) by using this uncooked version of the food 2 times per day as a breakfast and lunch or breakfast and dinner for her and using Vitamin C daily. THE DOCTORS COULD NOT DO THAT IN 1½ years! I add more greens for the 1 lymph node that is hard to reduce in size. It helps. This is a food and a drug version that is able to be used for Exhibit A. I have been using the ingredients as food to remove and calm her Attention Deficit Disorder issues for years without caffeine and only adding cocoa and caffeine sometimes and only as food.

This is the Actual Best Method I Use Every Day or as an Extremely Strong Continual Medicine

THE BEST DAILY METHOD of Diane Brooks FOR EXHIBIT A Symptoms

1 Favorite BEST METHOD and a $2^{nd}$ Semi-Favorite Best Method (This one is the only one I would use if I had my choice. It is the only one that I would Call my Best if I was allowed to pick just one favorite of my 8000 pages of combinations and recipes. It can be used by itself or add Pharmaceuticals into it before cooking it or after it or just eat 1 Ibuprofen with it)

4 Tablespoons Blonde Sesame Seeds (You can use Blonde sesame seeds) I used Spice Islands Sesame seeds. (Regular plain not ground seed. Grinding it makes a different potency and you must consider this. 2 Tablespoons not ground seed is better for me. If I want a stronger drug I use 3-4 tablespoons. 2 Best method: use 4 Tablespoons Black sesame seeds. Grind them with the rice.

2 Stash Green Tea bags: Place 2 cups of water and the green tea bags in microwave. Cook 10 minutes. Let set 20 minutes (smash or squeeze once). Remove the actual tea (bags) and only use the dark green tea water. (Cook up to 2 tablespoons of green tea for higher potency. Reduce tea quantity for a lower potency. I prefer less than $¾^{th}$ tablespoon or less of green tea used since I am a coffee drinker. I lower my coffee drinking to 2 cups of medium to light coffee in the morning and 1 cup at night. Too much intake of coffee makes this medicine too strong for me.) 2 Best method: Boil 6½ tsps of green tea (The cheap kind IMPRA Tea Global Brands 100 tea bags×1 g each in box. Empty the contents of the tea bags into a tsp measuring spoon 6 times) in 4 cups of water 18 minutes (or more or less depending on microwave) in microwave. Let set 15 to 30 minutes. Look for brown or dark water. That is best. Drain and use green tea water only. Discard actual tea. $¼^{th}$ tsp Olive Oil (Interchangeable with Evening Primrose oil). 2 Best method: 2 tsp of Olive Oil.

2 Tablespoons frozen green beans Place petite frozen green beans in a tablespoon container and do not smash down to make solid. Just use the green beans in the tablespoon. You do not want too many greens or it will push out the medicinal or narcotic effect and cause extreme imbalances. You need these greens to help remove illness. Greens detoxify you. (To make a narcotic effect medicine and a great medicine with very little hallucinations, use only a little greens.) For easy bump removal and toxin and cancer removal, add more than 2 tsps greens and only add enough to keep moods balanced. Too many greens and you lose mind and mood balancing effects. 2 Best method: ¼th cup frozen regular cut green beans. Just place them in frozen. Use as above.

½ cup rice Semi-ground, Powderize or grind the rice for best results. I prefer plain white or long grain tan rice in my recipe. Grind the rice with the sesame seeds in a coffee grinder. 2 Best method: $½^{th}$ cup of plain white rice. Grind the rice with the sesame seeds in a coffee grinder. 2 Tablespoons Sharp Cheddar cheese (I use Tillamook sharp cheddar cheese. Medium cheese can be used.) 2 Best method: 2½ to $2¾^{th}$'s Tablespoons Tillamook Sharp cheese. Use whole milk.

Add 4 cups of milk, stir and cook until almost dry. 2 Best method: 4 cups milk.
Add 4 cups of milk, stir and cook until almost dry. 2 Best method: 4 Cups milk.
Add 4 cups of milk, stir and cook until almost dry. 2 Best method: 4 Cups milk.
Add 4 cups of milk, stir and cook until almost dry. 2 Best method: 4 Cups milk.
Add 4 cups of milk, stir and cook until almost dry. 2 Best method: 4 Cups milk.
Add 4 cups of milk, stir and cook until almost dry. 2 Best method: 4 Cups milk.
Add 4 cups of milk, stir and cook until almost dry. 2 Best method: 4 Cups milk.

Be careful. The more you cook it, the fumes may intoxicate you.

Let set to dry or freeze. If dried, it will store outside a freezer. I usually keep it almost dried and freeze it and just take my daily portion from the freezer. (I usually quit here, but you can add 1 cup or 10 cups of milk for better medicines. Add more milk and keep cooking it for potency and doses to be changed)

I always consume my daily dose with 12 ounces of hot milk in the morning. It is important that you consume ½ tsp to 2 tablespoons of oil per day as a regular daily dose. I take 1 cup to ½ cup of oil or less every day with 1 cup of this medicine as my daily dose of medicine until I lower the dose to 1 tablespoon or a little more per day of each. I lower the dose of each after my body has been acclimated to this drug. I would prefer to just skip the oil. (Only a little oil is needed but this drug needs oil and if the foods you eat push out the oil, then consume more). Do it with your daily dose. You need it. It keeps the food from getting out of control in the body. I always have about 2 cups of coffee first in the morning or after a dose.

Take 1-2 cups of this per day (for days) in the morning with hot milk. (add oil). Then lower your dose. You can just eat ½ to $¼^{th}$ cup to cups per day, then reduce the daily dose to a tablespoon or 2 or more or less daily (with hot milk in the morning) or quit taking this period (only if you took oil with this.). Do this repeatedly until your whole body is acclimated or filled. You can add meat to this medicine. Then lower the dose to 1 tablespoon or less or more per day (depending on how many times you add milk and process it.) Take this daily in the morning with hot milk. This is my favorite way to consume this food. I get imbalances when I eat Pad That in large doses or too much of one thing and need to eat more of the medicine to reregulate myself. I also drink hot coffee with a $⅓^{rd}$ cup of hot milk. This works great and balancing my medicine. It takes 1-3 weeks to balance.

As with many medicines, the first 5-10 days (approximately) of balancing this in your body may cause some psychosis. You will notice that it almost completely disappears shortly after this initial body acclimation period. Your brain and body has to regulate this. No big deal.

Now, there are many ways to do this, but 2 are important:
1. Keep consuming a daily medicine dose with a little oil and hot milk.
2. Stop taking it after you have accustomed your body to this medicine.

It is a continual medicine.

After I have regulated this food recipe in my body, I consume normal food and never too much of one ingredient. Just keep your diet in balance. I find I cannot eat cheese as a snack unless it is balanced with other foods or it will cause a temporary psychosis. I drink 3 sips of evaporated milk if I drink too much coffee.

You just need to eat normal foods and not too much of one ingredient. I decrease my coffee consumption on my above dose to 2 cups of coffee in the morning and one at night. If I am too high (maybe I used too much of a sesame seed or caffeine in my recipe), I can eat a few more greens. Be careful on the quantity of greens as only a little is needed. Just go and eat another dose of the uncooked food version.

You will balance your medicine this way.

My favorite way to do this is to drink coffee and eat 1 tablespoon with hot milk every morning (and more or less if my symptoms break through.)

You need to keep taking this medicine until your body is filled so if you quit consuming the medicine, the medicine will continue.

I always drink hot coffee in the morning to stir up my medicine and make this medicine balanced. I stop drinking coffee (and I drink more if I need it) if the medicine is too strong. This is for the coffee addict: I use a medium strength coffee. Do not use strong coffee. If you have strong coffee, mix it with ½ water or use ½ the amount to make the pot of coffee. This is a general guideline and not mandatory with the Best methods listed here. You make an imbalanced drug if you consume strong coffee all day with these best methods.

Uncooked Version

Uncooked and Processed Inside the Human or Animal Body Best Method as a Cancer, Exhibit A, Bump, Toxin and Other Illness Remover (Non-Narcotic)

Eat these Ingredients Separately or Combine them and Eat for Breakfast 1 cup cooked rice (this is the only ingredient that is cooked. It is NOT cooked with the other ingredients)
4-6 little fat cut frozen green beans
1 tsp cheese (sharp preferred)
1 cup milk
1 pinch sesame seeds
4 tsps+ of olive oil
Cook 4 green tea bags in $¾^{th}$ cup of water. Let set. Put in the refrigerator and use only a little tea water in this recipe per day. Blend in blender. Cook in microwave 50 seconds and serve to the sick. Serve this exact meal as breakfast and lunch. Make 2 batches. This I rarely have severe cold or illness symptoms on this. You are purging the cells. You will notice your urine stinks. This is good. Do this for many days then just use as a daily purge. These ingredients are all in this patent and the claims in this patent are true. They remove toxins, cancer and debris. You should do this to remove illness. You can also do this recipe and only take ½ tsp of the above my favorite recipe and it will help detoxify your old recipe if you took one. I use it to balance my strong drugs. It removes strong imbalances and places a food inside the body that continually removes cancer and lymph node problems and handles exhibit A. You do not need caffeine. Please just use a little more green plant. I eliminate the green tea for myself. I just drink coffee daily. I try to limit my coffee intake. You can add vitamin C (vitamin ingredients in my patent), brownies (ingredients in this patent) to motivate your child to eat it and even stir in sugar for taste.

I eat these ingredients combined in some way every day. The interchangeable ingredients are in me continually every single day and have been since the month I was diagnosed with Lymph Node cancer exactly 4 years ago. If you have been diagnosed with cancer. Use this patent. You can use this on illness. It will push out many illness symptoms, cells, and works to push out illness and disease no matter what the problem, try it. Micah eats this one.

This works on MANY illness symptoms.

Uncooked Version for when I am overdosing on a strong drug or having a drug imbalance or am in need of a balancing food to add to my Cooked versions of the best Methods. It also is just a stabilizing food that can be eaten if you are not on a drug and need to slowly get off these best methods. It is a low potency version of the ingredients that helps people stabilize safely. I use this.
$⅓^{rd}$ cup cooked rice
$¾^{th}$ of a teaspoon of olive oil
2 short ¾ths inch pieces of green bean (It doesn't require much)

¾ths of a tsp of sharp cheddar cheese
¾ths cup Whole Milk
¼th tsp sesame seeds (I used Blonde one)
1 cup of coffee as a drink when you wake up and maybe another Combine these ingredients and place in a cup (You can drink the hot coffee separate) and heat in the microwave 1 minute and 22 seconds. Just until hot. Consume as a food or breakfast.

This will help eliminate hallucinations or narcotic effects or side effects from narcotics.

My Favorite Best Method

For People Who do not Need High Potency
Anti-Psychotics (which is not Me. I Need Stronger Ones)

1½ tsp blonde sesame seeds (or grind them).
1 tsp green tea in 2 cups water boiled until semi brown, let set. Drain the tea water and discard the tea. Use only the tea water.
½ tsp Wesson oil
¼th cup plain ground rice (or Grind the rice and the sesame seeds together in a grinder for so the oil in the sesame seeds don't clog the coffee grinder.)
1½ Tablespoons Tillamook Sharp Cheese
¼th cup frozen green beans. (Do not grind. Grinding changes the drug.)
12 cups milk (Do not use low fat milk. Whole milk is what I use) Combine all. Cook either on the stove stirring constantly or in a microwave or in the stove at 350 degrees. Cook until done. Place in little chunks in a baggie labeled MEDICINE DO NOT EAT and store in freezer and use. (The reason I write do not eat is so everyone knows it is a medicine.)

I eat this medicine the same as above. I use cups at first with oil and always with hot milk (and preferably with 2 cups of coffee in the morning) to regulate myself. Then after many days, I lower the dose to ½ cups then to tablespoon or less (but always with 1 tsp to tablespoon+ of oil daily). Remove the coffee or lower the coffee or caffeine intake if you are trying to take this drug to reduce the potency after being on a drug with higher sesame seed count and higher caffeine count.

These can be Added

Adjusting the coffee or daily caffeine count drastically changes this drug. If you need a little extra increase in potency, drink a cup of coffee before bed. I add a little cream. A glass of wine is good also, but may push out the medicinal effect in the morning. The coffee will greatly help. You will notice that when you wake up, you will feel medicated. A glass of Half & Half or a richer milk, taken before bedtime, is a wonderful way to help this medicine.

Add meat and many other additional ingredients in this patent to enhance this drug. If I get a little psychosis entering in, I eat a little meat. When I was just using the sesame seed/green tea/milk best methods, I would eat crawfish for a week and notice an increased medicated effect. It works on my best methods.

NOTICE: It may take you weeks to see that this medicine is regulated in you. Do not judge it while you are taking cups or more than a tablespoon per day with oil. You must be regulated to experience the medicine in the best form.

This medicine is my breakfast. After 2 cups of coffee in the am, I have a ¾ths of a tablespoon with about 14 ounces of hot milk. Then later in the morning I eat balanced food. I eat a little fruit and try to stay off greens and not eat too much meat. This is how I balance my foods. The best way is to never eat too much of any ingredient. I consume coffee only as needed (after my approximate 3 cups in the morning.)

Exhibit H

Prior Art (Letter to the Patent Office: This is a nutshell of my patent. The Prior art is just 2 examples of recipes that do not have these exact attributes. I made those 3 years ago and they are nothing compared to what is in this patent. They are weak and no strong narcotic effect. They do not have the capacity to do the job correctly. I wouldn't take them. They are simply not good enough. This patent I am filing is. Here is a background of the invention filed today:

Background of the Invention Diane's Manna:

This medicine is a interchangeable continual drug made from 1 to 7 interchangeable ingredients that heals and alleviates the symptoms of many illnesses including cancer and mental illness and pain and many others with the unique benefit it can be combined with medicines like Zyprexa with the benefit of this combination lasting months with a extremely strong, narcotic in nature medicinal benefit for over 21 days. Although please understand, I don't need to add Zyprexa or Ibuprofen to this medicine because it is good enough to do the job without adding any medicine to it. These ingredients include green plants that are interchangeable, small seeds that are interchangeable, green tea that is interchangeable with other ingredients such as coffee and narcotic seeds.)

So, The following Prior art is extremely different than the above paragraph)

PRIOR ART

The Bible. Communion. Feast of Unleavened Bread. Manna from Exodus.

Document: In the Communion recipe listed as patent 269-270 please note that only this recipe in my patent docs is prior art and the accompanying patent numbers have never been published. (It is not strong enough for many issues. Flour is wheat only.) I only released the benefits and claims are numbers 1-17 and that is all on page Unleavened bread and wine. It is a sample of one distinct recipe and has no strong narcotic seed in it, no green plants, no caffeine which are inherent in this unique patent I am filing.

Document: Media release Media 2 release provided recipe

New York Times ad (to publish the recipe in Communion recipe above and the second recipe) Seaweed, by itself, is for ADD.

Green Beans, by itself, is good for ADD.

Narcotic, by itself, is Moss. My journeys have provided this.

Vaccine: You need a small amount of mold. I made mold and created mold in Flour made of bleached wheat. I ate it. I then got deathly ill. It was a very deadly drug. The mold was in me and I thought it was a vaccine.

Evening primrose Oil is a stopper for mold. It actually did not stop the mold. I just thought it did.

As a healing of my cancer, I used evening primrose oil. This oil only is prior art. (Take 1 gallon and cook at extreme temperatures and freeze (Place oil freezer overnight). Repeat cooking it and freezing it 4-10 times. Use as needed.) This one Evening primrose oil is only allowed as prior art for cancer and an oil used in the vaccine and baking soda is a stopper. This ingredient "oil" by itself is prior art. It does ever include the variations I added into this patent and not the cooking, processing or the plant itself.

A stopper (something to stop any adverse affects to a vaccine) is Baking soda. It causes psychosis. The only prior art stopper is baking soda. (I have many ways to stop this medicine from continuing and this is one.)

Communion in the Holy Bible is Unleavened Bread and wine. Exodus clearly explains Unleavened bread. Wheat, water, oil and possibly a little salt is the biblical recipe made as cake. I changed this so uniquely that this is simply one way of many to remove toxins in the body.

Genesis 1 29:30 All green plants and fruit with seed in it is to be for food. Plants as patentable, but they are all listed in the bible as Green plants. Manna is described as many other things and mine is not. In Genesis, The Bible has the whole plant kingdom.

http://biblesays.faithsite.com/content.asp?CID=101890

Letter To President (communion recipe is a basic recipe that does not have my parts to this patent filing, but is a gift to the world. My children who are sick should be allowed this. God Bless you all.)

Media 1 Communion Recipe 2 pages
Letter For Government Mental Health Jan. 29, 2009
Another Disclaimer
Media 2 Recipe 4 pages
Silver (I heard someone say it is a cure.)

Exhibit I

This is a Statement of Use

I have Symptoms in Exhibit A (Except for the Few of Micah's)

This Medicine Works on the Symptoms.

Micah has Bumps or tumors in neck in child; undiagnosed Lymph node illness in child; Diagnosed lymph node illness in child. Her Issues are those and issues and illnesses are in Exhibit A and B for Micah Brooks. I used all the ingredients listed in Exhibits D, F, G, H. Micah only used the Uncooked Version and the ingredients in Exhibit G and some other seeds and greens in her morning oatmeal. When I say uncooked version, I am referring to Exhibit G and cooking the seeds and only heating the other ingredients in the microwave with the seeds for 50 seconds. She has also used many variable recipes for her Attention Deficit Disorder Symptoms. Micah has Attention Disorder Symptoms and also cannot handle sugar. Sugar makes her temporarily insane. The ingredients mixture in this patent removes this problem. If I place too many greens in her foods, the psychosis is back. Exhibit G, the uncooked version was used as breakfast and lunch for Micah for 2 (possibly 2 weeks and 2-3 days) and I completely eliminated a 1½ inch hard tumor like bump on her jaw and the bumps on her right side of her neck. She only had one bump left on her left side and an itty bitty remaining bump on her right side, almost unnoticeable after treatment. I then stopped using the uncooked version on her. Her neck was previously covered in bumps. She went to a MD and a Pediatric Surgeon for 1½ years and they could not remove the bumps. They said they were Lymph nodes. I did it in 2 weeks.

I have been diagnosed with many illnesses included in Exhibit A & B. The Exhibit for symptoms is Exhibit A. I wrote down all my symptoms and problems and diagnosis's for you to prove.

II completely subdued my mood issues. I have no mood disorder at all on my patent. You can easily say that works. Many variations of this patent work on these mood issues. Some recipes that do not have seed last only a few hours. The Recipes with seed, especially rice, last a long time. I do not really know how long exactly. I stopped counting at 30 days. The recipes with little seeds that are black or brown are very potent when brewed with green tea and milk. I add these to my rice and I get a strong drug that eliminates my lip retardation. I sometimes notice that in the mornings my lip retardation might creep back up. After I drink a cup of coffee or two, it is gone again. When I use a low grade drug or a low sesame seed and green tea amount in my patent, my psychosis pops through and I immediately need to take a large dose of a stronger best method. I have used all of these and made one that works best, my favorites in Exhibit G and D. There are many varieties and I need a strong one. I am very sick. I have visual impairments and can watch the wall breathe if I am not medicated. These drugs virtually eliminate this. I have to have a strong sesame seed and caffeine in these drugs to medicate this problem. I would prefer a less strong drug like the last and final recipe in Exhibit G, but I must have the sesame seed and green tea at a strength that eliminates psychosis. The Last recipe in Exhibit G is for the other illnesses. People who are depressed would love it. Poof, no depression. I have had anger problems in my life, zero thought focus or balance, rapid eye movements that could never focus on a dot and a severe reading problem. My mind would fly from thought to thought and I simply had the symptoms in Exhibit A. My whole body was retarded at one point and I kept video of that. The Psychologist never listened to me when I said My lip was jerking or retarded. Actually she listened but since I was already seeing a Psychiatrist, she did nothing about it. The Psychiatrist dissed it. When my lip went into a severe different spasm over Risperdal, he labeled it Tardive Dysconesia and that was his diagnosis. I stopped using Risperdal and the family of those drugs when my leg spasms were out of control. It was way more than that. The retardation was there for before I saw him. I could never sit still and was hyper all my life and no formal diagnosis of Bi-Polar until 2002-2003. The formal Diagnosis was Bi-Polar disorder. A previous diagnosis that a pastor psychologist and his crew diagnosed me with was Multiple Personality Disorder. They were wrong. You must understand Psychosis to see that maybe they picked the wrong page in the DSM. These pastors had no real training and the ones who diagnosed me told me I had been satanically ritually abused when I was too young to remember. Please know that I sued them for this. Another man, who was on the same training staff as this Pastor is being sued for harming another person and his family this way. The man I sued for my MPD Diagnosis, had his license revoked in 2003 in The State of Oregon Case #BCT2001-0006 for another case in Jul. 12, 2001. He trained pastors how to make MPD some spiritual issue and made his clients all believe they were gang raped when they were children. There is a video of his deposition that proves his mind control belief systems. There are many victims of his and his colleagues and these families were all harmed.

My symptoms are listed in Exhibit A. This patent was used by me in many ways as Exhibit C explains. I am very sick. This drug is interchangeable. I can interchange the ingredients to get the same results with different ingredients. I will show you that the symptoms and illnesses in Exhibit A can easily be eradicated, helped, sedated, fueled, medicated, given analgesic benefit to, given narcotic benefit to, removed, alleviated, regulated, solved, pushed out, pushed out toxins, burned, decreased, penetrated, stabilized, improved, anesthetized, slowed down, desensitized, corrected, vaccinated, changed, detoxifying, reduced, fed and benefited. In Exhibit A, you will see many symptoms that can be classified as mood disorders, mind disorders, physical disorders, pain disorders, bone issues and many disease problems that can be classified in many illness names and types. You can literally name many diseases and still solve their problems with this patent. I have. I have tested all of these. I have listed everything that this patent helps or handles in this paragraph above. It is a pretty long checklist.

The only issue that is not perfectly eradicated (in this patent) is my reading or semi-dyslexic reading or typing disorder. I can smooth it out by adding more greens, but then it detoxifies me and the medicinal value that solves my other problems is too adversely affected, so I live with an imperfect reading and typing disorder. It is not so bad that I cannot read. I just speed read or follow the methods in speed reading to grasp the material.

For 4 full years. I used a milk and bark cooked method, a milk and green tea and bark method, a seed and all my interchangeable ingredients and oil method, and all my interchangeable ingredients to eliminate my cancer in my body. It was a steady daily dose of these ingredients. The only time I did not use a daily dose was when I was testing the continuation drug. It just continued in me. I removed the cancer this way. I do this daily. It is a daily removal of cancer.

I have had chronic, severe 3 day headaches all my life and back pain since college. I have had the headaches since I was two. They last for 3 days. They were so severe I wouldn't be able to move without excruciating pain. Before my monthly period, these headaches would come and if I did any workout. I am 49. I do not have back pain or headaches now unless I change my medicines to a low sesame seed and caffeine formula.

I have no Premenstrual or menopause symptoms except mild hot flashes. I have no mood disorder.

I physically was sick. I did meth in 2000. I did cocaine that same year. This is the year I got severely mentally sick. It took a few years to get diagnosed and it was diagnosed as Bi-Polar. I used illegal drugs in my lifetime, but not severely. I drank alcohol, but was never an alcoholic. I just need you to know that even people who have harmed their bodies with these drugs that you may have severely harmed yourself and this, patent helps. If you have harmed your body with the chemicals and toxins in meth or any other substance that you have put in your body, USE THIS PATENT. It will detoxify you. This patent will heal you.

I have visual impairments and have found that I need a little cheese and a little wine. You should try it. It is in my best methods. The patent can be made without these ingredients, but I need them.

I have balanced the best methods to make a drug that works for my symptoms, all of them. I made these for me. I use them and they work. I eat my favorite best method daily. I do this in the morning and have to be sane. If I am on a low sesame seed or caffeine in my recipe, I get mentally sick and have to raise the seed level to My favorite best methods to regulate myself. It takes up to 10 days to do this. I take these and I have proven it works on Exhibit A's symptoms and illnesses. It has also worked on Micah. These recipes can be used on anyone. I have used them on a child and myself. I used the uncooked versions on my child. I also cook hers as morning oatmeal.

These food ingredients have been tested in the areas of Exhibit A. They work. The ingredient list in Exhibit F can be used instead of the ingredients in Exhibit G and D.

Specification Extras

<Example: I refused my surgery for Lymph Node cancer. The doctor wanted to take my all my upper Lymph nodes, a spot on my thyroid, and remove my tonsils and anything else he felt he needed to remove. I refused surgery, chemotherapy and radiation for cancer to find the primary origin of a removed fast growing tumor 4 years ago and treated myself with this patent. I have virtually eliminated my mood disorder. I have almost completely eliminated my lip retardation. I have greatly reduced delusions. I rarely have pain. I had back and neck pain for 25 years. I almost never have back pain now. I almost completely eliminated my headaches that I have had since I was 2. I have no noticeable Premenstrual syndrome symptoms or Menopause symptoms (except mild hot flashes) and mood swings have disappeared. I can stare at a dot for a long time and haven't had any rapid thoughts since I have been on these medicines. My focus disorder is gone. I am relaxed with no hyper activity disorder. My mind is stabilized and this medicine is a great mind stabilizer. Many symptoms are listed in Exhibit A. The pain is able to be managed with 1 Best method. You remove toxins and illness by using these ingredients.>

The ingredients in this patent combine with other patents, patentable ingredients, unpatented combinations, non-food or food ingredients, other foods or non-foods, medicines, other combinations of substituted foods and ingredients, other ingredients, other plants, seed, seed derivatives, shrubs or trees or living organism, therefore making new drugs, food, combination of foods, combination of food ingredients, combination of any combination, medicines, combination of ingredients, combinations of plant parts or plants to fulfill the claims in this patent.

It will push out illness, virus, cholesterol, blockages, toxins, cancer cells, and works to push out illness or disease.

Different seeds and seed derivatives, plants, green plants and parts, seed oil, oil, seed parts, earth ingredients, drugs, medicines, organism and human and animal body fluids and parts and derivatives can be used for this patent.

<Example: many ingredients and interchanged ingredients in Exhibit F. You may also get a list of all the healing properties of herbs and plants and roots, etc and just add them into this patent and create a new variation. Explanation: Exhibit F is an example of many different ones. Everyone I sampled worked. There are too many different seeds and seed derivatives on this planet. You should sample all of them. This patent claims that I am only providing a small sample and many different ones can be used. Each ingredient is inherently different.>

The uniqueness is that this patent is seed or is derived from seed.

The interchangeable ways to use this patent and the interchangeable ingredients in this patent are able to heal the body and reduce the symptoms of many illnesses.

A Recipe is to Add milk with seeds or seed derivatives or plants (and caffeine) and agitate it, blend it, cook it and you will make a stronger, more potent food.

<example is 12 sheets of Green Seaweed for sushi squares and 1 gallon of milk. Place in blender and blend until an even color. Cook it until dry. Another example is instead of using Seaweed, use $1/4^{th}$ to $1/2$ container of Spice Islands Sesame seeds (or Dark Brown Fir Bark water) instead of Green seaweed. Add the gallon of milk and cook until dry. Consume with hot milk>

Add caffeine and milk with seeds or seed derivatives or plants then agitate it, blend it, cook it and you will make a stronger, more potent food.

<example is 12 sheets of Green Seaweed for sushi squares. Cook 2 tablespoons of green tea in 3 cups of water. Cook the tea until the water is dark. Use only the green tea water and discard the tea. Combine the green seaweed and the gallon of milk and the green tea water and blend it until an even color. Cook it until dry. Consume with hot milk. Now, instead of using Seaweed, use $1/4^{th}$ to $1/2$ container of Spice Islands Black sesame seeds (or Dark Brown Fir Bark water) instead of Green seaweed. Add the green tea water and the milk and cook until dry. Consume with hot milk.>

Claim: These interchangeable ingredients operate inside a continuum.

<example: The Human body is a continuum that uses a heart and blood flow to continually move this medicine throughout the human body.>

Claim: These interchangeable ingredients fulfill the claims of this patent inside a continuum. The ingredients in this patent are used as a fuel source to make energy. <example: Food ingredients are used for energy in the human body. Food can be converted into energy. Example: Ethanol.>

By using Pharmaceutical prescription drugs or non-prescription drugs or ingredients or other combinations of ingredients in this medicine and processing it, the Pharmaceutical drug or non-pharmaceutical drug or added ingredients last much longer than it would by itself and you will need a far less quantity to get the same effects. This drug is an easy way to use much less of the Pharmaceutical drugs and other medicines, and other patents than they would use to get the same benefits when added to this patent.

Once you normalize the person, simply stop taking it and it will continue.

Another example is just add small amounts into your best methods. Another example is just add small amounts of the above medicines as this drug continuous in you to maintain your medicinal needs. (Then you do not need the excessive drugs in your medicine as the benefits will 1. continue or another way is 2. Lower the amount in the best methods or 3. Make it a Continual medicine and just add small amounts to maintain the dosage thus lowering the cost of Pharmaceutical drugs.) This patent has the ability to make Drugs less expensive will make my drugs more appealing to the people. (The Dr's had me on $800 per month mood stabilizers.)>

Claim: You may combine other foods, interchangeable ingredients, medicines, herbal remedies, and other already with this food.

These Interchangeable ingredients can be processed many ways to achieve the claims in this patent. <See Best Method Example in Exhibit D and G and in the Exhibits.>

Claim: It is a New Interchangeable FOOD Combination for Illness Treatment.

<Example: You need to look at my food and the combination and quantities as a grouping of unique ingredients that can be interchanged. This is a way to treat illness. In Home economics in Junior High I was taught the old basic food groups. This is a New Food Group Combinations matter. Potencies Matter and best of all SEED matters. This is the new f food group. Each ingredient interacts with the other ingredients a certain way. You will find these quantities to work as a best method.

CLAIM: This patent rebukes cancer, cancer cells, and kills cancer.

<Explanation:

I can remove cancer by a perfectly balanced food that includes milk. I take my basic recipe and I add a processed potent oil and this recipe is used to burn cancer out of my body. Olive Oil is used and Primrose Oil have been used. You do not need to use Chemotherapy. You need to burn it out and then let it burn inside at a normal human body heat with a certain mix of ingredients that remove the cancer. This process is continual. These medicines have an oil and milk. I used Evening primrose oil. Olive Oil is a substitute for Evening Primrose Oil and it makes the mental health and pain medication continue as well as the anti-cancer food. I have been on this for $3 1/2$ years since my Lymph node $1 1/2$ inch tumor was cut out and the doctor said it was not the place of origin. The doctors immediately scheduled me for my entire neck cut open second surgery, all upper lymph nodes gutted out, tonsils and thyroid surgery, chemotherapy demand and radiation was strongly demanded. I refused all of their treatments. Take a best method and drink 1 cup of Evening Primrose oils cooked at extreme temperatures then placed in a freezer. Do this 4 times. Then eat or drink this oil for days with the Best Method. This will purge your cells and place the food medicine throughout your body. It is wise to use it this way for best results. This recipe is the one I used and can be varied with olive oil, moss, and it is better to include the whole Evening Primrose plant including the root system. I have used all of these methods. Treat yourself daily to the best method recipe and gradually decrease the oil until you have leveled off to 1 tsp per day of this oil. That is how you treat malignancy or cancer. Cancer patients need daily oil treated like this and the interchangeable best method. You need to remove the cells as you treat the cancer. This treatment is a wonderful daily treatment and a wonderful way to remove it. I don't use extra oil anymore. I just use the best method. I am alive from something that was sure to kill me. The ingredients push out toxins.

Evening Primrose oils that have been heated and cooled numerous times gave me a mild to medium psychosis and mild body aches. After the initial strong doses, I lowered the doses to 1 tsp of the oils per day with the interchangeable ingredients to my patent and have kept them in my body. After about 18 months, I stopped taking 1 tsp per day of oil and just use the tiny amount in the 1 best method. I used a cancer drug mixed with a special food processed to eliminate the cancer from my body. The elimination is a seed pounding out the cancer cells and I am alive. If I was dying of cancer, I would go eat cups of the 4× processed Evening Primrose Oil and the 1 Best method recipe and then lower the doses, but still keep as much oil in me as I could stand. It is much better to just push out toxins and cancer with the food combinations (use the evening primrose plant).

Another Way is to Continually Use the Best Methods to Remove Cancer Cells.>

Interchangeability example is copy seed for seed and other plant based seeds or plants for plants, and green plant for plants, tea for coffee or other substitutes, cheese for ripe fruit, and cheese for wine and oil for oil and caffeine does not need to be added.

A small adjustment in ingredients changes the medicine.

<Explanation: 2 examples are 1. A small adjustment in Sesame seed or its interchangeable ingredients changes the drug. 2. A small change in caffeine or its interchangeable ingredients changes the drug. 3 Tablespoons of Sesame seeds and $1 3/4^{th}$'s tablespoons to 2 tablespoons of Green tea is a much stronger drug than 2 tablespoons of sesame seeds and $3/4^{th}$ tablespoon of green tea. (Testing this in the 1 best method shows this.) I do not like strong medicines that do not allow me normal day-to-day energy and enthusiasm. The higher doses of these above ingredients cause me to not to operate at my normal energy level. I prefer the lower doses. If the dose is too low (not enough caffeine or sesame seed) the medicine is not strong enough for me. (An example for a too low dose for me is 1 tablespoon or less of sesame seeds and less than $1/2$ green tea bag or none used in 1 best method). I prefer the higher doses for acute issues and acute pain.)>

The ingredients in this patent can be used as detoxification. The ingredients in this patent, seed, milk, rice, grains, greens, cheese, and its' substitutes can be used as a detoxification. Explanation: When I use a 1 best method that has 3 Tablespoons of sesame seeds and 1½ Tablespoons of Green tea in it and I use it as directed, It is difficult to detoxify. I must either use full recipe doses of a 1 best method with 2 Tablespoons (Or less) of sesame seeds and ¾ths tablespoon (or less) of green tea in my 1 best method recipe and take large initial daily doses to move out the old recipe or THE BEST METHOD: Eat 2 cups (to 1 cup) of cooked rice with 2 tsps of green beans, 1 tsp of aged cheese and 12 ounces of hot milk every day until the old medicine has been removed. The latter can cause Detoxification symptoms including psychosis and body pain. You can also add 1 tsp of a cooked sesame seed/green tea/milk best method recipe to the plain cooked rice, cheese, greens, milk recipe to calm this effect.>

This drug will continue operating inside the body.

Oil is used for the reason of making this medicine continue in a safe and effective manner. Green plants mixed with caffeine and milk ingredients or their substitutes are used to make this medicine effective. Green plants in a drug is good for detoxification. You can add cheese to reduce delusions and psychosis issues and other Visual or other mental impairments such as any delusion. Seed and seed derivatives moving through the body helps remove retardation and stroke symptoms. <Explanation: I use a rice seed in my best method to remove my retardation symptoms. It works almost perfectly on me. I would say 99% effective but I know in a patent I shouldn't be so percentage (okay 99.9% effective) specific. The sesame seed cooked with green tea and milk does not successfully remove my lip retardation. I added rice and green plants and oil to maximize the removal of my stroke symptoms. (Please know the retardation or Parkinson's disease symptoms or even a block in a CNS or cholesterol issues are reduced substantially while on this Food.) Seeds that are like Rice can be used.>

Seeds and seed derivatives for the mixtures help keep this long term in the body. <Explanation: Rice and the ingredients in 1 the best method for this.>

If overdosing or on a drug or a combination of this patent that is too potent, remove or reduce the caffeine and sesame seeds and purge out the excess with cups of cooked rice and green plants. You can also use milk and a little cheese for a better balanced food.

Cooking these ingredients increases potency. <Example: The Best methods ingredients are made more potent by cooking the ingredients at 2-4 cup milk addition intervals. It increases potency. It also will cause you to get high if you are cooking it like this. It is stronger when you cook it to semi-dry status or dry status like the recipe says with each successive cooking of milk> Seeds mixed with caffeine and milk products are a very potent drug. These interchanged ingredients push out malignant cells and toxins. There are many ways and processes to utilize this Interchangeable Patent. <Please refer to Exhibit C> There are many ways to process this Interchangeable Patent. <Please refer to Exhibit C and E> Potency and strength and quality can be maximized and increased many ways.

This patent is a narcotic effect food and a narcotic effect medicine.

The interchangeable ways to use this patent and the interchangeable ingredients in this patent are able to reduce the symptoms of many illnesses continually.

SUMMARY

This Interchangeable medicine heals the body, Benefits, feeds, reduces, detoxifies, Increases or decreases in potency, decreases illness, Increases or decreases in strength, changes, Anesthetizes, slows down, Relaxes, Improves, Stabilizes, Relieves, medicates, continues or not continues, continues in a continuum, a food continues or not continues, decreases, burns, pushes out, removes, regulates, sedates, fuels, gives Analgesic benefit, gives Narcotic benefit, and Alleviates the symptoms and what is listed in Exhibit A and Exhibit B Doctor list with interchangeable food, interchangeable processed ingredients, interchangeable pharmaceutical drugs, interchangeable non-pharmaceutical drugs, interchangeable combined Pharmaceutical drugs with these interchangeable ingredients, interchangeable plants, interchangeable seeds, interchangeable Derivatives of Seed, interchangeable organism or human fluids and interchangeable parts, earth ingredients, sub-classes of patents, interchangeable processes, interchangeable methods of use, interchangeable uses, that are Interchangeable and each have their own individual uses, combined uses, methods of use, methods of ingestion, claims and benefits interchangeable healings.

The invention claimed is:

1. A method of treating a human suffering from cancer, pain, and Bipolar disorder consisting essentially of administering to said human therapeutically effective amounts of evening primrose oil, rice, sesame seeds, green beans, coffee, meat, cheese, milk, green tea extract, evening primrose seeds, and wine.

* * * * *